(12) United States Patent
Pohl

(10) Patent No.: US 10,379,090 B2
(45) Date of Patent: Aug. 13, 2019

(54) CHARGE REVERSIBLE ION EXCHANGE RESINS, CHROMATOGRAPHY COLUMN, METHOD, AND SYSTEM THEREOF

(71) Applicant: DIONEX CORPORATION, Sunnyvale, CA (US)

(72) Inventor: Christopher A. Pohl, Union City, CA (US)

(73) Assignee: Dionex Corporation, Sunnyvale, CA (US)

(*) Notice: Subject to any disclaimer, the term of this patent is extended or adjusted under 35 U.S.C. 154(b) by 269 days.

(21) Appl. No.: 15/186,258

(22) Filed: Jun. 17, 2016

(65) Prior Publication Data

US 2017/0363592 A1     Dec. 21, 2017

(51) Int. Cl.
| | |
|---|---|
| *G01N 30/96* | (2006.01) |
| *B01J 39/26* | (2006.01) |
| *B01J 39/20* | (2006.01) |
| *B01D 15/36* | (2006.01) |
| *B01J 41/14* | (2006.01) |
| *B01J 41/20* | (2006.01) |
| *B01J 20/30* | (2006.01) |
| *B01J 39/05* | (2017.01) |
| *B01J 41/05* | (2017.01) |
| *B01D 15/16* | (2006.01) |

(52) U.S. Cl.
CPC ............ *G01N 30/96* (2013.01); *B01D 15/361* (2013.01); *B01J 20/3071* (2013.01); *B01J 39/05* (2017.01); *B01J 39/20* (2013.01); *B01J 39/26* (2013.01); *B01J 41/05* (2017.01); *B01J 41/14* (2013.01); *B01J 41/20* (2013.01)

(58) Field of Classification Search
CPC .............................. G01N 30/96; B01D 15/168
See application file for complete search history.

(56) References Cited

U.S. PATENT DOCUMENTS

| | | |
|---|---|---|
| 5,281,631 A | 1/1994 | Horwitz et al. |
| 5,503,933 A | 4/1996 | Afeyan et al. |

(Continued)

FOREIGN PATENT DOCUMENTS

| | | |
|---|---|---|
| CN | 104190480 A | 12/2014 |
| CN | 104619416 A | 5/2015 |

(Continued)

OTHER PUBLICATIONS

Dionex IonPac CS19 Columns, Product Manual, P/N: 065440-02, Jun. 2012, 59 pages.

(Continued)

*Primary Examiner* — Ryan B Huang
(74) *Attorney, Agent, or Firm* — Timothy J. Ohara

(57) ABSTRACT

An ion exchange chromatographic packing material is described that includes a copolymer grafted to support resin particles. The copolymer includes an ion exchange group, an ionic crosslinking group configured to ionically bind to the ion exchange group, and an adjustable ionization state group having at least a first net charge at the first pH and a second net charge at the second pH. An overall first net charge of the chromatographic packing material at the first pH is opposite in polarity to the overall second net charge of the chromatographic packing material. This allows impurities to be removed from the chromatographic packing material at the second pH.

38 Claims, 12 Drawing Sheets

(56) References Cited

U.S. PATENT DOCUMENTS

| | | | |
|---|---|---|---|
| 5,712,347 | A | 1/1998 | Trochimcznk et al. |
| 5,783,608 | A * | 7/1998 | Sugo ................. B01D 39/1623 521/29 |
| 5,865,994 | A | 2/1999 | Riviello et al. |
| 5,925,253 | A | 7/1999 | Pohl et al. |
| 5,936,003 | A | 8/1999 | Pohl et al. |
| 5,968,363 | A | 10/1999 | Riviello et al. |
| 6,248,798 | B1 * | 6/2001 | Slingsby .............. B01D 15/363 210/661 |
| 6,544,484 | B1 | 4/2003 | Kaufman et al. |
| 6,568,245 | B2 | 5/2003 | Kaufman |
| 6,857,295 | B2 | 2/2005 | Hansen et al. |
| 7,147,891 | B2 | 12/2006 | Bordunov et al. |
| 7,166,226 | B2 | 1/2007 | Woodruff et al. |
| 9,169,331 | B2 | 10/2015 | Liu et al. |
| 9,310,344 | B2 | 4/2016 | Liu et al. |
| 9,486,799 | B2 | 11/2016 | Pohl |
| 2009/0218238 | A1 | 9/2009 | Dasgupta et al. |
| 2011/0117626 | A1 * | 5/2011 | Komkova ................. C08J 3/246 435/206 |

FOREIGN PATENT DOCUMENTS

| | | | |
|---|---|---|---|
| EP | 2745904 A1 * | 6/2014 | ......... B01D 15/3847 |
| EP | 2745904 A1 | 6/2014 | |

OTHER PUBLICATIONS

Dionex Product Manual for IonPac(R) CG12A IonPac(R) CS12A, Doc No. 031132, Rev. 09, May 2010, 78 pages.

HPLC 2015 Abstract HYP-TH-0-09:20, Pohl et al., "New hybrid mode cation-exchange column for use in HPLC and ion chromatography," Jun. 2015, 3 pages.

Rey, "Novel cation-exchange stationary phase for the separation of amines and of six common inorganic cations," J. of Chrom., 739, 1, 87-97, 1996.

Examination report dated Apr. 8, 2018, to EP Patent Application No. 17176468.1.

* cited by examiner

CHARGE REVERSIBLE ION EXCHANGE RESINS, CHROMATOGRAPHY COLUMN, METHOD, AND SYSTEM THEREOF

FIELD OF THE INVENTION

The field of the invention relates to chromatographic packing material or resins for applications such as ion chromatography, liquid chromatography, and high pressure liquid chromatography.

BACKGROUND

Chromatography is a widely used analytical technique for the chemical analysis and separation of molecules. Chromatography involves the separation of one or more analyte species from other matrix component present in a sample. A stationary phase of a chromatography column is typically selected so that there is an interaction with the analyte. Such interactions can be ionic, hydrophilic, hydrophobic, or combinations thereof. For example, the stationary phase can be derivatized with ionic moieties that ideally will bind to ionic analytes and matrix components with varying levels of affinity. A mobile phase is percolated through the stationary phase and competes with the analyte and matrix components for binding to the ionic moieties. The mobile phase or eluent are terms used to describe a liquid solvent or buffer solution that is pumped into a chromatography column inlet. During this competition, the analyte and matrix components will elute off of the stationary phase as a function of time and then be subsequently detected at a detector. Examples of some typical detectors are a conductivity detector, a UV-VIS spectrophotometer, and a mass spectrometer. Over the years, chromatography has developed into a powerful analytical tool that is useful for creating a healthier, cleaner, and safer environment where complex sample mixtures can be separated and analyzed for various industries such as water quality, environmental monitoring, food analysis, pharmaceutical, and biotechnology.

Stationary phase synthesis methods may utilize grafting for attaching ion exchange sites to the surface of a substrate. Such materials have been used for many commercial ion exchange products. Other stationary phase synthesis methods may utilize a crosslinker for forming bulk ion exchange resins. One parameter used to adjust selectivity in bulk ion exchange resins is the mole percent of crosslinker. Applicant believes that there is a need to use a crosslinker in a grafting process to improve selectivity in grafted stationary phases. Under certain circumstances, the use of a covalent crosslinker is not possible during a normal graft processes due to the fact that a covalent crosslinker causes gelation of the graft solution. Applicant also believes that gel formation is irreversible and incompatible with a grafting process for manufacturing useful chromatographic stationary phases.

Applicant also believes that there is a need to provide stationary phases that can be cleaned of impurities should they become fouled. For example, a stationary phase designed for separation of small mono, di, and trivalent ions is often exposed to samples containing polymeric ions of the same net charge. Such polymeric ions tend to form a very strong complex with the stationary phase which can be extremely difficult to remove once the complex is formed. Stationary phases can be ultimately destroyed due to excessive exposure to polymeric or other highly charged species.

SUMMARY

A first embodiment of an ion exchange chromatographic packing material includes support resin particles and a copolymer grafted to the support resin particles. The copolymer includes an ion exchange group, an ionic crosslinking group, and an adjustable ionization state group. The ion exchange group is configured to have a polarity that does not change when switching from a first pH to a second pH, in which the first pH and the second pH are different. The ion exchange group, the ionic crosslinking group, and the adjustable ionization state group are different. The ionic crosslinking group is configured to ionically bind to the ion exchange group. The adjustable ionization state group having at least a first net charge at the first pH and a second net charge at the second pH in which the first net charge and the second net charge are different. An overall first net charge of the chromatographic packing material at the first pH is opposite in polarity to the overall second net charge of the chromatographic packing material.

In regards to the first embodiment of the ion exchange chromatographic packing material, the ion exchange group includes a cation exchange group and the adjustable ionization state group includes a zwitterionic group, in which a mole percent of the ionic crosslinker group is less than a mole percent of the ion exchange group.

In regards to any of the above embodiments of the ion exchange chromatographic packing material, the ion exchange group includes a cation exchange group and the adjustable ionization state group includes a zwitterionic group, in which a mole percent of the ionic crosslinker group is less than a mole percent of the adjustable ionization state group.

In regards to any of the above embodiments of the ion exchange chromatographic packing material, the ion exchange group includes a cation exchange group and the adjustable ionization state group includes a zwitterionic group, in which a mole summation of the ionic crosslinking group and the adjustable ionization state group is greater than a mole amount of the ion exchange group.

In regards to any of the above embodiments of the ion exchange chromatographic packing material, a mole percent of the ion exchange group ranges from (or about) 5% to (or about) 49%, a mole percent of the ionic crosslinking group ranges from (or about) 5% to (or about) 40%, and a mole percent of the adjustable ionization state group ranges from (or about) 10% to (or about) 90%.

In regards to any of the above embodiments of the ion exchange chromatographic packing material, the mole percent of the ion exchange group is (or about) 40%, the mole percent of the ionic crosslinking group is (or about) 20%, and the mole percent of the adjustable ionization state group is (or about) 40%.

In regards to any of the above embodiments of the ion exchange chromatographic packing material, the ion exchange group includes an ion exchange monomer that has been polymerized, in which the ion exchange monomer is selected from the group consisting of a styrene sulfonate, a vinyltoluene sulfonate, a vinylnaphthalene sulfonate, a 2-sulfoethyl methacrylate, a 3-sulfopropyl methacrylate, a 2-acrylamido-2-methylpropane sulfonate, and a combination thereof.

In regards to any of the above embodiments of the ion exchange chromatographic packing material, the ionic crosslinking group includes an ionic crosslinking monomer that has been polymerized, in which the ionic crosslinking monomer is selected from the group consisting of a vinylbenzyltrimethylammonium, vinylbenzyldimethylethylammonium, vinylbenzylmethyldiethylammonium, vinylbenzyldimethylethanolammonium, vinylbenzylmethyldiethanolammonium, vinylbenzyltriethylammonium, vinylbenzyltriethanolammonium, vinylbenzyltripropylammonium, 2-acryloxyethyltrimethylammonium chloride, diallyldimethylammonium chloride, 2-methacryloxyethyltrimethylammonium chloride, methacryloylcholine methyl sulfate, and a combination thereof.

In regards to any of the above embodiments of the ion exchange chromatographic packing material, the ionic crosslinking group includes a quaternary amine.

In regards to any of the above embodiments of the ion exchange chromatographic packing material, the adjustable ionization state group includes an adjustable ionization state monomer that has been polymerized, in which the adjustable ionization state monomer is selected from the group consisting of vinylbenyzldimethylglycine, vinylbenyzldimethylaminopropionic acid, vinylbenyzldimethylaminobutyric acid, and a combination thereof.

In regards to any of the above embodiments of the ion exchange chromatographic packing material, the zwitterionic group includes a benzyl group, a dimethylglycine group, in which an amine group of the dimethylglycine group is quaternized.

In regards to any of the above embodiments of the ion exchange chromatographic packing material, the first net charge of the adjustable ionization state group is neutral and in which the second net charge of the adjustable ionization state group is positive where the overall second net charge of the chromatographic packing material is positive at the second pH.

In regards to any of the above embodiments of the ion exchange chromatographic packing material, the ion exchange group includes a sulfonate group, the ionic crosslinking group includes a quaternary amine group, and the adjustable ionization state group includes a quaternary amine and a carboxylate group.

In regards to any of the above embodiments of the ion exchange chromatographic packing material, the ion exchange group includes a phosphonate group, the ionic crosslinking group includes a quaternary amine group, and the adjustable ionization state group includes a quaternary amine and a carboxylate group.

In regards to any of the above embodiments of the ion exchange chromatographic packing material, the second pH ranges from (or about) zero to (or about) one.

In regards to any of the above embodiments of the ion exchange chromatographic packing material, the first pH ranges from (or about) 1.5 to (or about) 3.

In regards to any of the above embodiments of the ion exchange chromatographic packing material, the at least one copolymer has a linear structure and is tethered to the support resin particle.

In regards to any of the above embodiments of the ion exchange chromatographic packing material, the at least one copolymer has a non-uniform distribution of the ion exchange groups, the ionic crosslinking groups, and the adjustable ionization groups.

In regards to any of the above embodiments of the ion exchange chromatographic packing material, the at least one copolymer has a first portion proximate to a tethered region where the at least one copolymer is tethered to the support resin particle, in which the at least one copolymer has a second portion proximate to a terminus region of the copolymer, in which a concentration of the ionic crosslinking groups is greater in the second portion than the first portion.

In regards to any of the above embodiments of the ion exchange chromatographic packing material, the copolymer includes at least three consecutively bound ionic crosslinking groups in the second portion.

In regards to the first embodiment, a second embodiment of the ion exchange chromatographic packing material includes the ion exchange group in the form of an anion exchange group, the first net charge of the adjustable ionization state group and the overall first net charge of the ion exchange chromatographic packing material have a same polarity.

In regards to the first and second embodiments, a third embodiment of the ion exchange chromatographic packing material includes the ion exchange group in the form of an anion exchange group and the adjustable ionization state group includes a positively charged group, in which a mole percent of the ionic crosslinker group is greater than a mole percent of the ion exchange group.

In regards to the first to third embodiments, a fourth embodiment of the ion exchange chromatographic packing material includes the ion exchange group in the form of an anion exchange group and the adjustable ionization state group includes a positively charged group, in which a mole summation of the anion exchange group and the adjustable ionization state group is greater than a mole amount of the ionic crosslinker group.

In regards to the first to fourth embodiments, a fifth embodiment of the ion exchange chromatographic packing material includes a mole percent of the ionic crosslinking monomer ranges from (or about) 20% to (or about) 80%, a mole percent of the ion exchange monomer ranges from (or about) 5% to (or about) 40%, and a mole percent of the adjustable ionization state monomer ranges from (or about) 10% to (or about) 90%.

In regards to the first to fifth embodiments, a sixth embodiment of the ion exchange chromatographic packing material includes a mole percent of the ionic crosslinking monomer is (or about) 40%, a mole percent of the ion exchange monomer ranges is (or about) 30%, and a mole percent of the adjustable ionization state monomer ranges is (or about) 30%.

In regards to the first to sixth embodiments, a seventh embodiment of the ion exchange chromatographic packing material includes the ion exchange group in the form of an anion exchange group. The anion exchange group includes a quaternary amine group. The ionic crosslinking group includes a sulfonate group. The adjustable ionization state group includes a guanidine group.

In regards to the first to seventh embodiments, an eighth embodiment of the ion exchange chromatographic packing material includes the first pH ranges from (or about) 11 to (or about) 13, and the second pH ranges from (or about) 13.5 to (or about) 14.5.

In regards to any of the above embodiments, the ion exchange chromatographic packing material includes at least one copolymer tethered to the support resin particle via an unreacted vinyl groups at the surface of the support resin particle. The copolymer forms a covalent bond to the unreacted vinyl group.

In regards to any of the above embodiments, the support resin particle includes a support copolymer. The support copolymer includes polymerized support monomers that include a divinylbenzene and an ethylvinylbenzene.

In regards to any of the above embodiments, the support resin particle includes (or about) a 55% by weight of divinylbenzene and (or about) 45% by weight of ethylvinylbenzene.

In regards to any of the above embodiments, the support resin particle includes a pore size range of (or about) 70 angstroms to (or about) 80 angstroms.

In regards to any of the above embodiments, the support resin particle includes a surface area of (or about) 450 square meters/gram.

In regards to any of the above embodiments, the support resin particle is approximately spherical with a diameter of 5 (or about) seven microns.

In an embodiment of a chromatography column, the column contains a packed bed of the ion exchange chromatographic packing material of any of the above embodiments.

A ninth embodiment of an ion exchange chromatographic packing material made by a method including combining a support resin particle, an ion exchange monomer, an ionic crosslinking monomer, and an adjustable ionization state monomer to form a reaction mixture. A copolymer is formed of the ion exchange monomer, the ionic crosslinking monomer, and the adjustable ionization state monomer. The copolymer is grafted to the support resin particle. A polarity of the ion exchange monomer does not change when switching from a first pH to a second pH, in which the first pH and the second pH are different. The ionic crosslinking monomer is configured to ionically bind to the ion exchange monomer. The adjustable ionization state monomer has at least a first net charge at the first pH and a second net charge at the second pH, where an overall first net charge of the chromatographic packing material at the first pH is opposite in polarity to the overall second net charge of the chromatographic packing material.

In regards to the ninth embodiments, the reaction mixture can include an initiator, an acid, and a perchlorate salt.

In regards to any of the above embodiments, a mole percent of the ion exchange group is a mole amount of the ion exchange group divided by a summation of the mole amount of the ion exchange group, a mole amount of the adjustable ionization state group, and a mole amount of the ionic crosslinker group; and multiplied by 100.

In regards to any of the above embodiments, a mole percent of the adjustable ionization state group is a mole amount of the adjustable ionization state group divided by a summation of the mole amount of the ion exchange group, a mole amount of the adjustable ionization state group, and a mole amount of the ionic crosslinker group; and multiplied by 100.

In regards to any of the above embodiments, a mole percent of the ionic crosslinker group is a mole amount of the ionic crosslinker group divided by a summation of the mole amount of the ion exchange group, a mole amount of the adjustable ionization state group, and a mole amount of the ionic crosslinker group; and multiplied by 100.

An embodiment of a method of separating an analyte includes flowing a first eluent having a first pH and containing a plug of a sample into a chromatography column containing a packed bed of the ion exchange chromatographic packing material of any of the above embodiments. The sample is separated into one or more analyte bands in the chromatography column. The one or more analyte bands are detected eluting off of the chromatography column.

In regards to the embodiment of the method of separating an analyte further, it includes flowing a second eluent with a second pH into the chromatography column. Next, an impurity is removed from the chromatographic packing material with the second eluent.

In regards to the embodiment of the method of separating an analyte further, the second eluent includes an organic solvent.

An embodiment for a system for chromatographically separating a sample includes a pump, an injection valve, a chromatography column containing a packed bed of the ion exchange chromatographic packing material of any of the above embodiments, and a detector.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

DETAILED DESCRIPTION OF EMBODIMENTS

Figure 1:
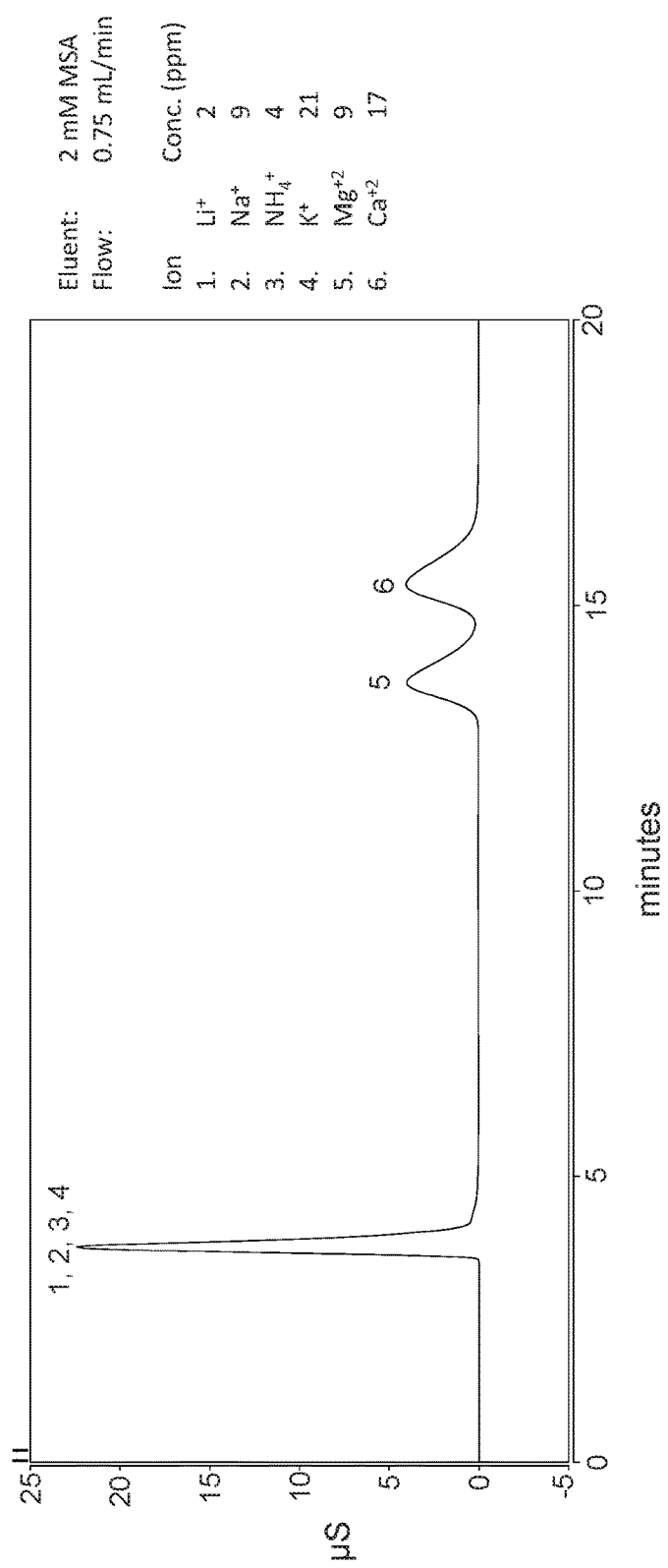
FIG. 1 shows a chromatogram of a sample containing 6 cations using a chromatography column containing a cation exchange packing material of Example 5 using a 2 mM methanesulfonic acid (MSA) eluent.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention. As used herein, the terms "about" or "approximately" for any numerical values or ranges indicate a suitable dimensional tolerance that allows the part or collection of components to function for its intended purpose as described herein.

A reversible ion exchange resin may include a combination of three different types of ionic sites such that under normal operating conditions. For cation exchange chromatography, a normal operating range for use with hydronium-based eluents may be between about pH 1 and about pH 3. For anion exchange chromatography, a normal operating range for use with hydroxide-based eluents may be between about pH 11 and about pH 13. However, other pH ranges might be of interest when operating with other eluents. For example, a useful pH range for anion exchange chromatography with a carbonate eluent system may be between about pH 9 and about pH 11. A reversible ion exchange resin has a net charge (either positive or negative) while under user controllable conditions for separating ions. However, the ionization state of one of the monomers can be altered so that the net charge of the ion exchange material is reversed. The three monomers may include a functional monomer (i.e. the monomer that provides retention sites during normal operation) such as a cation exchange monomer, the ionic cross-linking monomer which is present at a molar concentration less than the functional monomer and the adjustable ionization state monomer. The functional monomer may be an anion exchange monomer or a cation exchange monomer. For cation exchange, the adjustable ionization state monomer can be either neutral or zwitterionic (and thus net neutral) under normal conditions, but under a more extreme operating conditions can be converted into a charge state opposite that of the functional monomer. The total molar concentration of the adjustable ionization state monomer and the ionic cross-linking monomer are greater than the molar concentration of the functional monomer. The ionic cross-linking monomer allows for the incorporation of crosslinks in a grafted polymer. Using conventional cross-linking monomers is incompatible with grafting as it results in gelation of the graft solution. The adjustable ionization state monomer allows for easy regeneration of the ion exchange material to remove highly retained analytes which otherwise foul conventional ion exchange materials.

For example, the graft mixture could include a styrene sulfonate salt such as potassium styrene sulfonate (the functional monomer), a quaternary monomers such as vinyl-benzyltrimethylammonium chloride (the ionic cross-linking monomer) and a zwitterionic monomer such as vinylbenzyldimethylglycine (the adjustable ionization state monomer). If the mole percent of the three monomers is: 40 mole % potassium styrene sulfonate, 20 mole % vinylbenzyltrimethylammonium chloride and 40 mole % vinylbenzyldimethylglycine and the pH of the mobile phase is sufficiently high (e.g., the pH is 2-3), vinylbenzyldimethylglycine will be in its zwitterionic form, and thus, not affect the stationary phase net charge state. Under these conditions, the stationary phase will have a net negative charge since the mole % of the functional monomer is double the mole % of the ionic cross-linking monomer. By dropping the pH to 0-1, the carboxylic acid functional group associated with the vinylbenzyldimethylglycine will become protonated converting vinylbenzyldimethylglycine to its cationic form. Under these conditions, there will be a net excess of positive charge since 60 mole % of the monomer composition will be in a cationic state. Under these conditions, any cationic polymers which have formed a complex with the cation-exchange phase will be ejected from the stationary phase due to electrostatic repulsion. As a consequence the fouling polymer will be removed and the capacity of the stationary phase restored. Once this has been accomplished, the pH can be dropped to a pH suitable for cation-exchange chromatography and use of the column would be restored.

An ion exchange chromatographic packing material can include support resin particles and a copolymer grafted to the support resin particles. The following will describe the support resin particles that are suitable to use with the embodiments described herein. The support resin particle can be any inert substrate particle that is suitable for grafting with an ion exchange copolymer provided that the support resin is chemically stable under the intended conditions of use. In an embodiment, the support resin particle may be based on a divinylbenzene crosslinking monomer and a support resin monomer where the support resin monomer may be an ethylvinylbenzene monomer, a styrene monomer, and a combination thereof. The support resin particles may have a diameter ranging from about 1 micron to about 20 microns, preferably from about 2 microns to about 10 microns, and more preferably from about 3 microns to about 7 microns. The support resin particles may have a surface area ranging from about 20 $m^2/g$ to about 800 $m^2/g$, preferably from about 400 $m^2/g$ to about 800 $m^2/g$, more preferably from about 400 $m^2/g$ to about 500 $m^2/g$, and yet more preferably be about 450 $m^2/g$. The support resin particles may have a pore size ranging from about 70 angstroms to about 80 angstroms.

In an embodiment, the support resin particles include the divinylbenzene crosslinking monomer and the ethylvinylbenzene monomer. This support resin particle can be referred to as DVB. A mole percent of the divinylbenzene crosslinking monomer (% $DVB_{mole}$) is a mole amount of the divinylbenzene crosslinking monomer ($DVB_{mole}$) divided by a summation of the mole amount of the divinylbenzene crosslinking monomer ($DVB_{mole}$) and a mole amount of the ethylvinylbenzene monomer ($EVB_{mole}$), and multiplied by 100. The mole percent of the divinylbenzene crosslinking monomer may range from about 30% to about 90%, and preferably be about 55%. A mole percent of the ethylvinylbenzene monomer (% $EVB_{mole}$) is a mole amount of the ethylvinylbenzene monomer ($EVB_{mole}$) divided by a summation of the mole amount of the divinylbenzene crosslinking monomer ($DVB_{mole}$) and a mole amount of the ethylvinylbenzene monomer ($EVB_{mole}$), and multiplied by 100. The mole percent of the ethylvinylbenzene monomer may range from about 10% to about 70%, and preferably be about 45%. Alternatively, the support particles may be based on other vinylaromatic monomers such as alpha-methylstyrene, chlorostyrene, chloromethylstyrene, vinyltoluene, vinylnaphthalene, and a combination thereof. The support particles may also be based on unsaturated monomers, and copolymers of the above vinylaromatic monomers and unsaturated monomers. Preferably such monomers will be copolymerized with a vinylaromatic crosslinking monomer such as divinylbenzene but other vinylaromatic crosslinking monomers such as trivinylbenzene, divinylnaphthalene, and a combination thereof may also be used.

Now that the support particles have been described, the following will describe a copolymer and the process of making the copolymer. The copolymer includes polymerized functional monomers such as an ion exchange monomer, an ionic crosslinking monomer, and an adjustable ionization state monomer. The ion exchange monomer is configured to have a polarity that does not change when switching from a first pH to a second pH.

The ion exchange monomer can include an anion exchange monomers or a cation exchange monomers. Examples of anion exchange monomers may be a salt, solvate or hydrate of vinylbenzyltrimethylammonium, vinylbenzyldimethylethylammonium, vinylbenzylmethyldiethylammonium, vinylbenzyldimethylethanolammonium, vinylbenzylmethyldiethanolammonium, vinylbenzyltriethylammonium, vinylbenzyltriethanolammonium, vinylbenzyltripropylammonium, 2-acryloxyethyltrimethylammonium chloride, diallyldimethylammonium chloride, 2-methacryloxyethyltrimethylammonium chloride, methacryloylcholine methyl sulfate, and other suitable quaternary anion-exchange monomers derived from reaction of tertiary amines with vinylbenzyl chloride, with vinylbenzyl glycidyl ether, glycidylacrylate or glycidylmethacrylate and a combination thereof. It should be noted that the anion exchange monomers would be in the protonated and positively charged state at the first pH to bind to anionic analyte molecules, however, the anion exchange monomers may, under certain circumstances, be unprotonated and neutral during synthesis and/or cleaning. Further, the cation exchange monomers and/or groups may form an unprotonated neutral complex, a salt complex, solvates, or hydrates during storage.

Examples of cation exchange monomers may be a salt, solvate, or hydrate of styrene sulfonate, vinyltoluene sulfonate, vinylnaphthalene sulfonate, 2-sulfoethyl methacrylate, 3-sulfopropyl methacrylate, 2-acrylamido-2-methylpropane sulfonate, and a combination thereof. It should be noted that the cation exchange monomers would be in the unprotonated and negatively charged state at the first pH to bind to cationic analyte molecules, however, the cation exchange monomers may, under certain circumstances, be protonated during synthesis. Further, the cation exchange monomers and/or groups may form a salt complex, protonated neutral complex, solvates, or hydrates during storage. In the case of sulfonate, the ion exchange group maintains a negative polarity over a pH range of at least about 0 to about 14.

In addition to sulfonate groups, the ion exchange monomers may be a salt, solvate, or hydrate of a member including a phosphonate group. Examples of phosphonate monomers include vinylphosphonate, vinylbenzylphosphonate, 2-butenylphosphonate, vinyl(α-aminobenzyl)phosphonate], and a combination thereof.

In an embodiment where the ion exchange group is a cation exchange group, the first pH can be a range representing the pH range (e.g., 1.5 to 3) for performing a chromatographic separation whereas the second pH can be a value or range (e.g., 0 to 1) representing a pH for cleaning the chromatographic material. In this embodiment, the cation exchange group may include a sulfonate group.

The ionic crosslinking monomer is configured to ionically bind to the ion exchange monomer. The ionic crosslinking monomer may include a charged group that is oppositely charged to the ion exchange monomer allowing the ionic crosslinker monomer to bind to the ion exchange monomer. The ionic crosslinking monomer may crosslink to an ion exchange monomer on the same copolymer chain (intramolecular crosslinking) or another copolymer chain (intermolecular crosslinking). It should be noted that the use of an ionic crosslinking monomer during the grafting process as described herein results in ion exchange chromatographic packing material that does not form a gel and can separate a variety of ions.

Where the ion exchange group is a cation exchange group, the ionic crosslinking monomer can include a positively charged amine group and more particularly a quaternary amine group. For use with a copolymer including a cation exchange group, the ionic crosslinking monomer may be a salt, solvate, or hydrate of vinylbenzyltrimethylammonium, vinylbenzyldimethylammonium, vinylbenzylmethylammonium, vinylbenzyldimethylethylammonium, vinylbenzyldiethylammonium, vinylbenzylethylammonium, vinylbenzyldimethylethylammonium, vinylbenzylammonium, vinylbenzyldimethylethanolammonium, vinylbenzylmethyldiethanolammonium, vinylbenzyltriethylammonium, vinylbenzyltriethanolammonium, vinylbenzyltripropylammonium, 2-acryloxyethyltrimethylammonium chloride, 2-(N,N-dimethylamino)ethyl acrylate, N-[3-(N,N-dimethylamino)propyl] methacrylamide, 2-N-morpholinoethyl methacrylate, 3-dimethylaminoneopentyl acrylate, N-[3-(N,N-dimethylamino)propyl] acrylamide, 2-(N,N-diethylamino)ethyl methacrylate, 2-(tert-butylamino)ethyl methacrylate, 2-diisopropylaminoethyl methacrylate, N-(3-aminopropyl) methacrylamide hydrochloride, N-[2-(N,N-dimethylamino)ethyl]methacrylamide, 2-(N,N-dimethylamino)ethyl methacrylate, 2-aminoethyl methacrylate hydrochloride, N-(2-aminoethyl) methacrylamide hydrochloride, diallyldimethylammonium chloride, 2-methacryloxyethyltrimethylammonium chloride, methacryloylcholine methyl sulfate and a combination thereof.

For use with a copolymer including an anion exchange group, the ionic crosslinking monomer may be a salt, solvate, or hydrate of styrene sulfonate, vinyltoluene sulfonate, vinylnaphthalene sulfonate, 2-sulfoethyl methacrylate, 3-sulfopropyl methacrylate, 2-acrylamido-2-methylpropane sulfonate, vinylphosphonate, acrylate, methacrylate, vinylbenzoic acid, beta-carboxyethyl acrylate, and a combination thereof. It should be noted that the ionic crosslinking monomers that include weak acid carboxylate groups will bind to the anion exchange group when the pH is relatively high (so that the carboxylate is negatively charged).

For copolymers including a cation exchange group, the ionic crosslinking monomers would be in the protonated and positively charged state at the first pH so that it can bind to cation exchange monomers. However, the ionic crosslinking monomers may, under certain circumstances, be unprotonated during synthesis. Further, the ionic crosslinking monomers and/or groups may form a salt complex, solvates, or hydrates during storage.

For copolymers including an anion exchange group, the ionic crosslinking monomers would be in the unprotonated and negatively charged state at the first pH so that it can bind to anion exchange monomers. However, the ionic crosslinking monomers may, under certain circumstances, be protonated during synthesis.

The adjustable ionization state monomer has at least a first net charge at the first pH and a second net charge at the second pH. The adjustable ionization state monomer can allow an overall first net charge of the chromatographic packing material at the first pH to be opposite in polarity to the overall second net charge of the chromatographic packing material.

For example, cation exchange chromatographic packing material can include an adjustable ionization state monomer that may be a zwitterionic monomer in which the first net charge is neutral at the first pH. In an embodiment, a zwitterionic monomer can be vinylbenzyldimethylglycine where the nitrogen group is quaternized to form a positively charged group and the carboxylic acid group forms the negatively charged group. When switching to a second pH value of 0 to 1, the carboxylic acid group will become protonated, and thus, have a neutral charge whereas the quaternized nitrogen group will remain charged causing the adjustable ionization monomer to switch from a net neutral charge to a net positive charge. If the adjustable ionization monomer concentration is sufficiently high compared to the ion exchange monomer, then the overall net charge of the chromatographic packing material will have a positive polarity at the second pH. The overall net positive charge will cause all cations or a substantial amount (>50%) of the cations to not bind or be released from the chromatographic packing material. The adjustable ionization state monomer may be a salt, solvate, or hydrate of vinylbenyzldimethylglycine, vinylbenyzldimethylaminopropionic acid, vinylbenyzldimethylaminobutyric acid, vinylbenzyltetramethylguanidine, quaternary amino phosphonates and amine oxide monomers, and a combination thereof.

For example, anion exchange chromatographic packing material can include an adjustable ionization state monomer that can have a first net charge that is positive at the first pH. In an embodiment, an adjustable ionization state monomer can be vinylbenzyltetramethylguanidine where the imine group has a positive charge at the first pH, which may range from about 11 to about 13. When switching to a second pH value that may range from about 13.5 to about 14.5, the imine group will become unprotonated, and thus, have a neutral charge causing the adjustable ionization monomer to switch from a net positive charge to a net neutral charge. As a result, if the amount of ionic crosslinking group is greater than the amount of the anion exchange group, then the charge of the ionic crosslinking group will dominate causing the overall net charge of the chromatographic packing material to have a negative polarity at the second pH. The overall net negative charge will cause all anions or a substantial amount (>50%) of the anions to not bind or be released from the chromatographic packing material.

Figure 9:
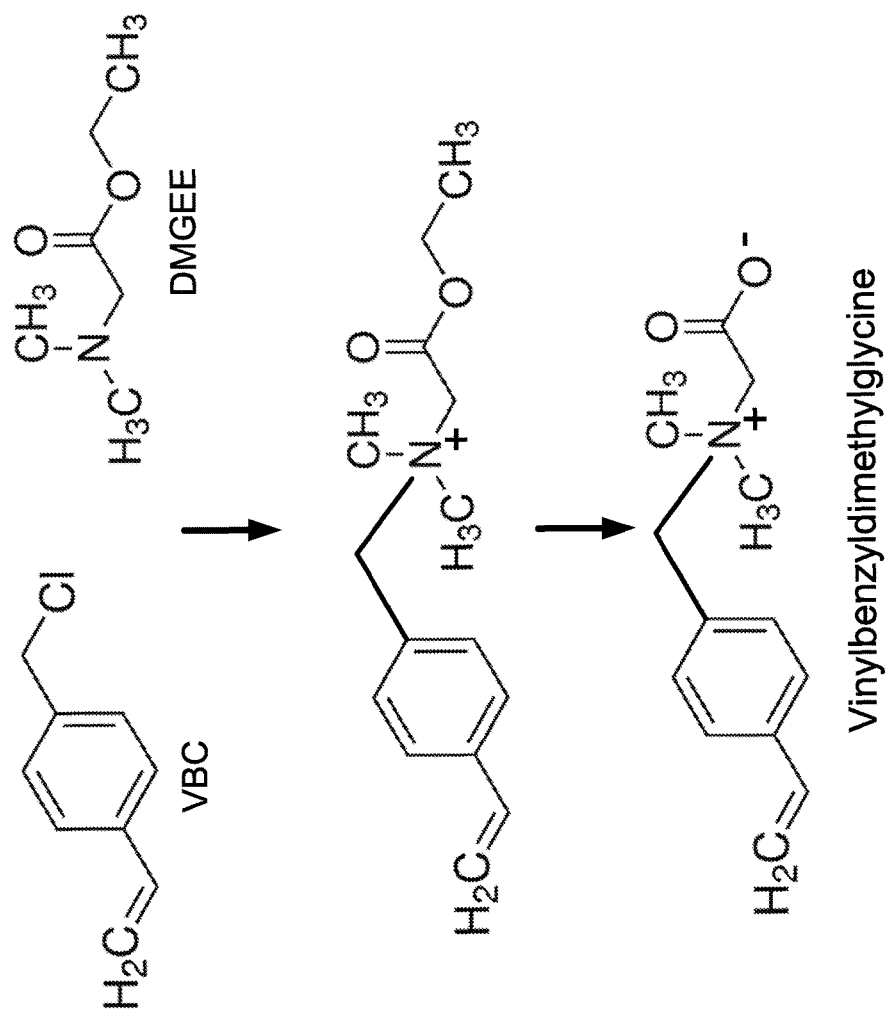
FIG. 9 is a schematic illustrating a synthesis of vinylbenzyldimethylglycine.

The adjustable ionization state monomer, vinylbenyzldimethylglycine, may be synthesized based on a schematic of FIG. 9. Vinylbenzyl chloride (VBC) can be reacted with dimethylglycine ethyl ester (DMGEE) to form vinylbenzyldimethylglycine ethyl ester. In this reaction, the chloride of VBC is displaced by the tertiary amine of DMGEE to form a quaternary amine. Next, the ester function is hydrolyzed with NaOH to form a carboxylate group as part of the vinylbenyzldimethylglycine. The resulting vinylbenyzldimethylglycine is a derivatized monomer that includes a benzyl group, a dimethylglycine group, in which an amine group of the dimethylglycine group is quaternized.

Figure 11:
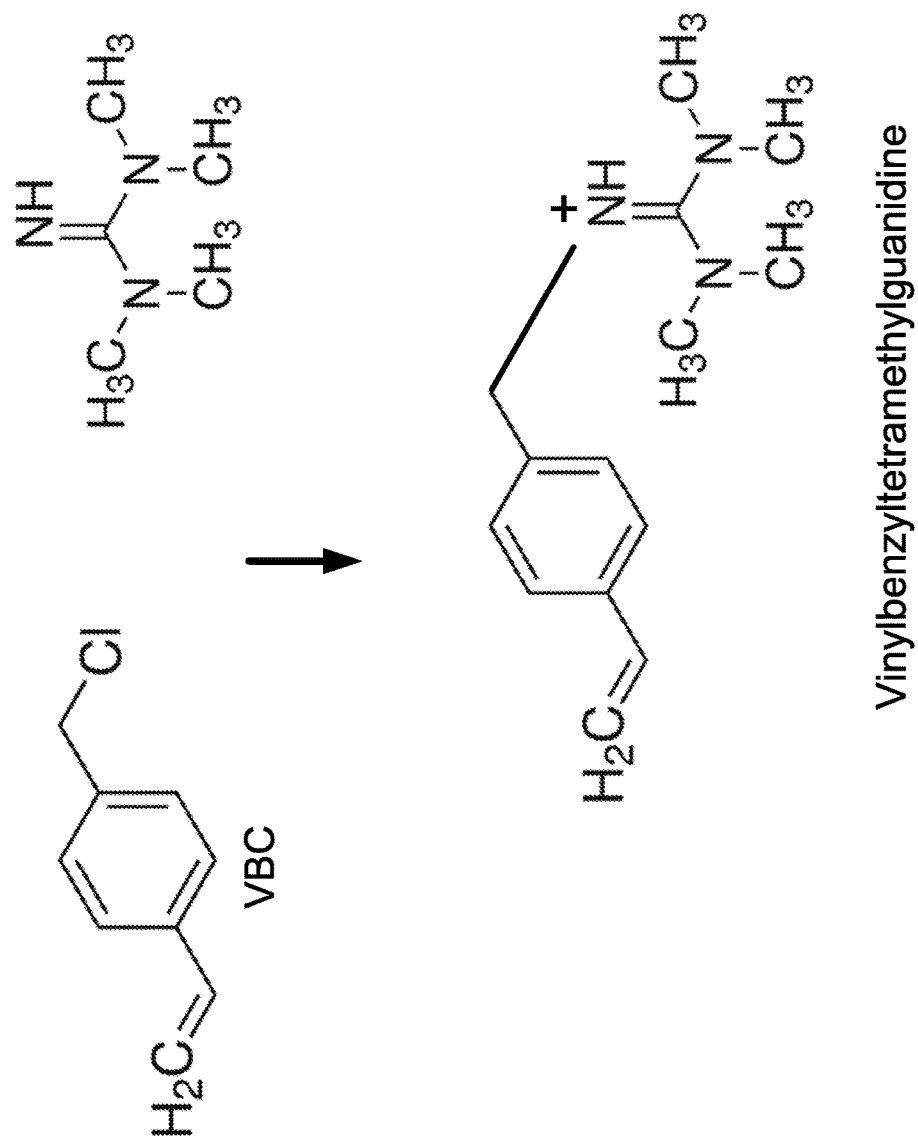
FIG. 11 is a schematic illustrating a synthesis of vinylbenzyltetramethylguanidine.

Another embodiment of an adjustable ionization state monomer with, vinylbenzyltetramethylglycine, may be synthesized based on a schematic of FIG. 11. 1,1,3,3-tetramethylguanidine can be reacted with vinylbenzylchloride to form vinylbenzyltetramethylguanidine. In this reaction, the chloride of VBC is displaced by the imine group of 1,1,3,3-tetramethylguanidine to form a covalent linkage. The resulting vinylbenzyltetramethylguanidine is a derivatized monomer that includes a benzyl group and a guanidine group. In an embodiment, vinylbenzyltetramethylguanidine is suitable for use in anion exchange chromatographic packing material. It should be noted that this adjustable ionization state monomer has a strongly basic group and can have either a positive or neutral charge.

Figure 12:
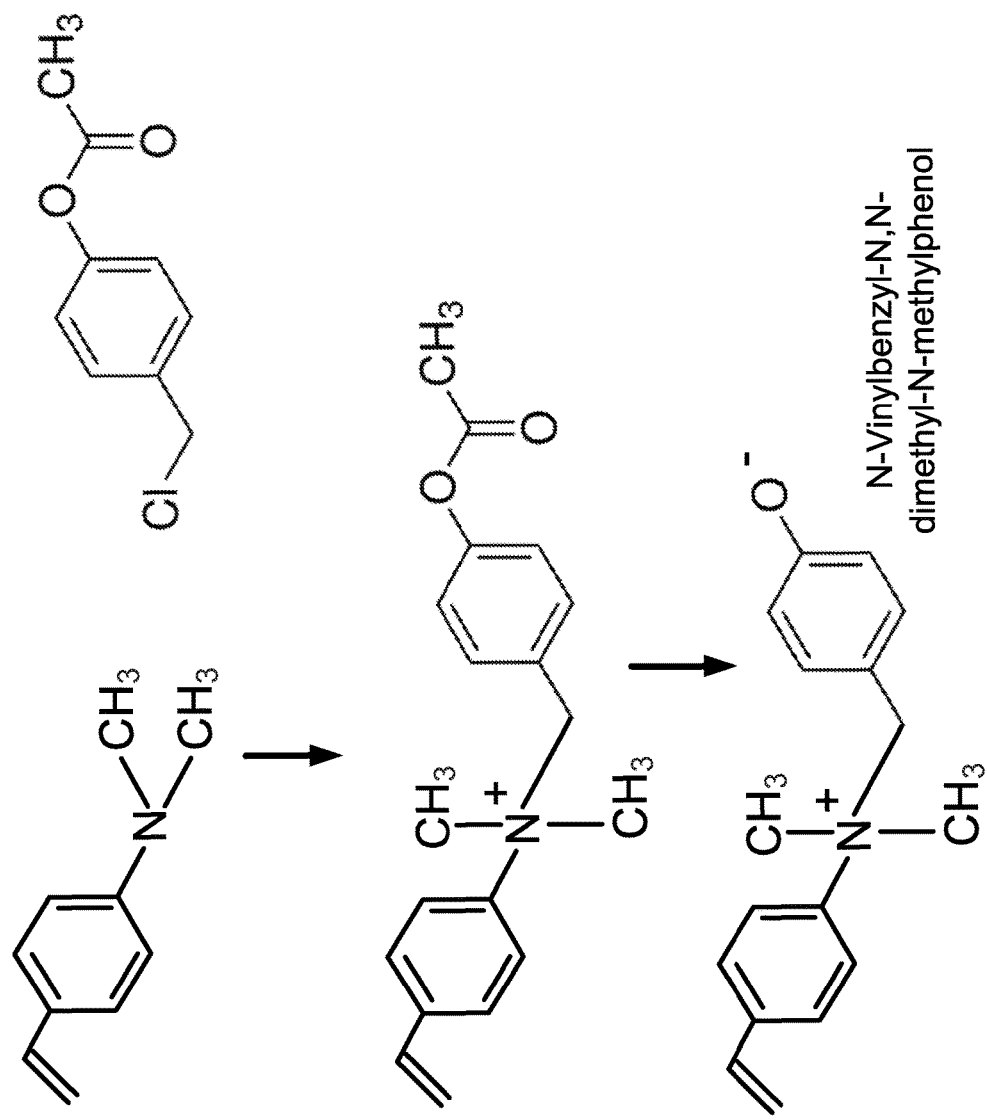
FIG. 12 is a schematic illustrating a synthesis of N-vinylbenzyl-N,N-dimethyl-N-methylphenol.

Another embodiment of an adjustable ionization state monomer is a phenolic zwitterionic monomer. For instance, N-vinylbenzyl-N,N-dimethyl-N-methylphenol, may be synthesized based on a schematic of FIG. 12. Vinylbenzyldimethylamine can be reacted with chloromethylphenylacetate to form N-vinylbenzyl-N,N-dimethyl-N-methylphenylacetate. In this reaction, the chloride of chloromethylphenylacetate is displaced by the tertiary amine of vinylbenzyldimethylamine to form a quaternary amine. Next, the ester function is hydrolyzed with NaOH to form a phenol group as part of the, N-Vinylbenzyl-N,N-dimethyl-N-methylphenol. The resulting N-vinylbenzyl-N,N-dimethyl-N-methylphenol is a derivatized monomer that includes a benzyl group, a methylphenol group, in which an amine group of the vinylbenzyldimethylamine group is quaternized. The phenol group can provide an advantage in that the pKa is a higher than a carboxylate group so control of ionization will be at a significantly higher pH that is compatible with the eluent pH typically used in anion exchange chromatography.

Figure 10:
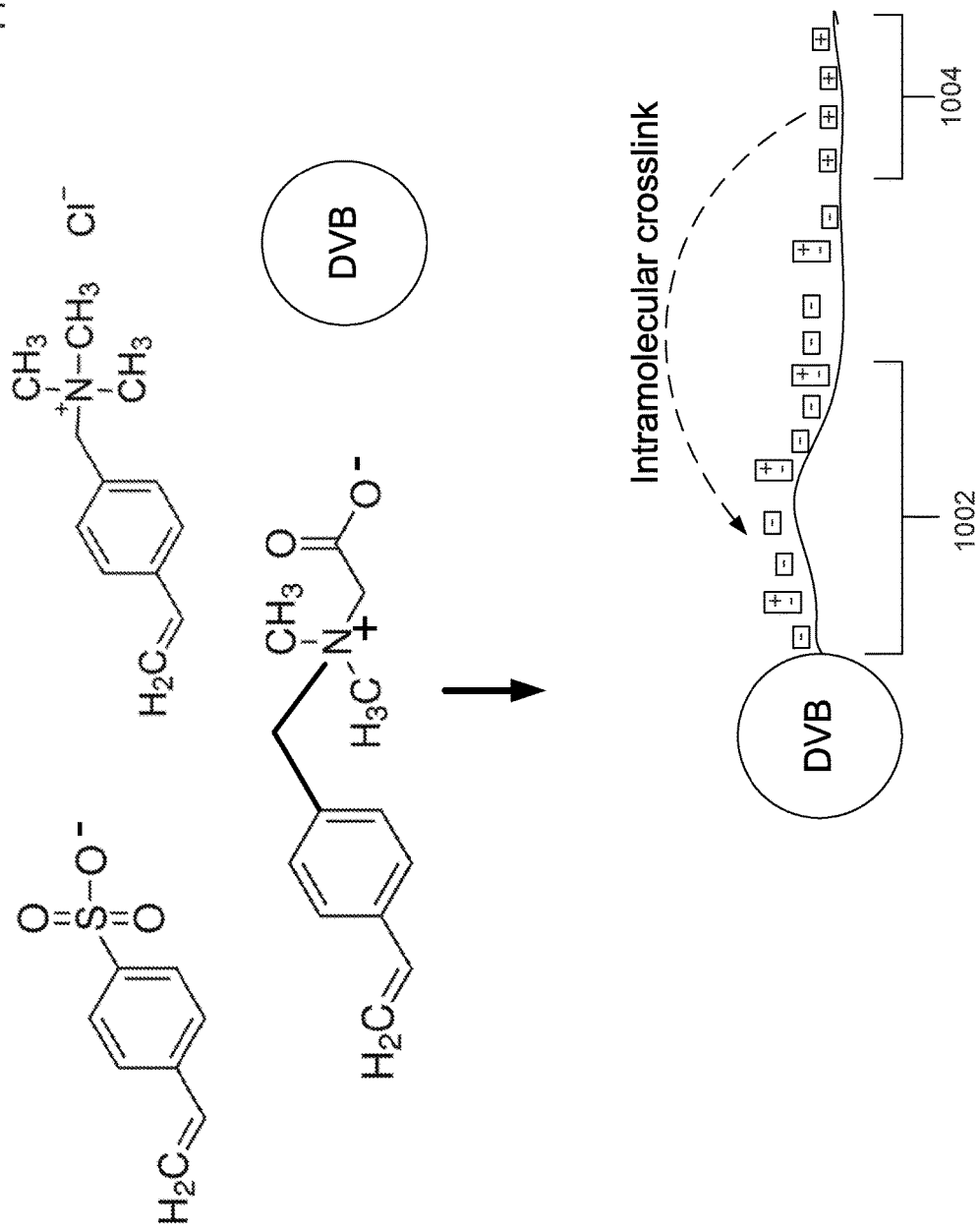
FIG. 10 is a simplified schematic illustrating a grafting of a copolymer to a DVB support resin particles made from divinylbenzene crosslinking monomer and the ethylvinylbenzene monomer.

FIG. 10 is a simplified schematic illustrating a grafting of a copolymer to a DVB support particle. A method of the ion exchange chromatographic packing material includes combining a support resin particle, an ion exchange monomer, an ionic crosslinking monomer, and an adjustable ionization state monomer to form a reaction mixture. The ion exchange monomer, the ionic crosslinking monomer, and the adjustable ionization state monomer can form a copolymer. In an embodiment, the copolymer can have linear structure as a result of the vinyl groups polymerizing together through a free-radical mechanism. This copolymer can then be grafted to the support resin particle. The surface of the support resin particle such as, for example, DVB particles may have unreacted vinyl groups that can tether to at least one end of the copolymer.

In an embodiment, the reaction mixture includes an acid and a perchlorate salt. The acid causes the reaction mixture to be acidic so that a hydroxide complex does not form with vinylbenzyltrimethylammonium and that the perchlorate salt forms. Without wishing to be bound by theory, Applicant believes that the perchlorate salt complex decreases the solubility of the vinylbenzyltrimethylammonium monomer causing the reactivity of the vinylbenzyltrimethylammonium to decrease during the polymerization. As a result, the vinylbenzyltrimethylammonium would be more likely to polymerize towards the end of the reaction process causing the positively charged vinylbenzyltrimethylammonium groups to have a higher concentration at the terminus of the copolymer as illustrated in FIG. 10. Since the styrene sulfonate and the vinylbenzyldimethylglycine would be more soluble in the presence of acid and perchlorate salt, Applicant believes that these two monomers would have a higher concentration at a region proximate to the surface of the support resin particle. The resulting copolymer has a first portion 1002 proximate to a tethered region where the at least one copolymer is tethered to the support resin particle as illustrated in FIG. 10. The resulting copolymer also has a second portion 1004 proximate to a terminus region of the copolymer such that a concentration of the ionic crosslinking monomer is greater in the second portion than the first portion as illustrated in FIG. 10. By decreasing the solubility of vinylbenzyltrimethylammonium with respect to the other two monomers, the copolymer will have a non-uniform distribution of these ion exchange monomers, which are the ionic crosslinking monomers and the adjustable ionization monomers. In an embodiment, the copolymer can include at least three consecutively bound ionic crosslinking monomers or more in the second portion 1004. As illustrated in FIG. 10, the ionic crosslinking group of the second portion 1004 forms an intramolecular ionic bond to the ion exchange group of the first portion 1002.

In an embodiment where the adjustable ionization state monomer is zwitterionic at the first pH and the ion exchange monomer is a cation exchange monomer, a mole percent of the ionic crosslinker may be less than a mole percent of the ion exchange monomer and/or a mole percent of the adjustable ionization state monomer. A mole percent of the ionic crosslinking monomer may range from about 5% to about 40%, and preferably be about 20%. A mole percent of the ion exchange monomer may range from about 5% to about 49%, and preferably be about 40%. A mole percent of the adjustable ionization state monomer may range from about 10% to about 90%, and preferably be about 40%. In this embodiment, the adjustable ionization state monomer can be net neutral and zwitterionic at the first pH, and be net positive or negative at the second pH.

In an embodiment where the adjustable ionization state monomer is positive at the first pH and the ion exchange monomer is an anion exchange monomer, a mole percent of the ionic crosslinker may be greater than a mole percent of the ion exchange monomer. A summation of a mole amount of the ion exchange monomer and the adjustable ionization state monomer can be greater than the ionic crosslinking monomer. A mole percent of the ionic crosslinking monomer may range from about 20% to about 80%, and preferably be about 40%. A mole percent of the ion exchange monomer may range from about 5% to about 40%, and preferably be about 30%. A mole percent of the adjustable ionization state monomer may range from about 10% to about 90%, and preferably be about 30%. In this embodiment, the adjustable ionization state monomer can be positive at the first pH, and be neutral at the second pH.

For reference, a mole percent of an ionic crosslinker monomer (% $ICM_{mole}$) is a mole amount of the ionic crosslinker monomer ($ICM_{mole}$) divided by a summation of a mole amount of the ionic crosslinker monomer ($ICM_{mole}$), an ion exchange monomer ($IXM_{mole}$), and an adjustable ionization state monomer ($AISM_{mole}$), and then multiplied by 100. A mole percent of an ion exchange monomer (% $IXM_{mole}$) is a mole amount of the ion exchange monomer ($IXM_{mole}$) divided by a summation of a mole amount of the ionic crosslinker monomer ($ICM_{mole}$), an ion exchange monomer ($IXM_{mole}$), and an adjustable ionization state monomer ($AISM_{mole}$), and then multiplied by 100. A mole percent of an adjustable ionization state monomer (% $AISM_{mole}$) is a mole amount of the adjustable ionization state monomer ($AISM_{mole}$) divided by a summation of a mole amount of the ionic crosslinker monomer ($ICM_{mole}$), an ion exchange monomer ($IXM_{mole}$), and an adjustable ionization state monomer ($AISM_{mole}$), and then multiplied by 100.

In a cation exchange embodiment, a mole summation of the ionic crosslinking monomer and the adjustable ionization state monomer is greater than a mole amount of the cation exchange monomer. Where the ionic crosslinking monomer and the adjustable ionization state monomer both have the same polarity at the second pH, this allows the second overall net charge of the ion exchange chromatographic packing material to be an opposite polarity of the first overall net charge of the ion exchange chromatographic packing material. In an embodiment, the first pH ranges from about 1.5 to about 3 and the second pH from about 0 to about 1.

In an embodiment, an ion exchange chromatographic packing material may be an anion exchange chromatographic packing material. In this embodiment, the anion exchange monomer can be vinylbenzyltrimethylammonium chloride, the adjustable ionization state monomer can be vinylbenzyltetramethylguanidine, and the ionic crosslinking monomer can be vinylstyrene sulfonate.

Removal of polymeric fouling agents can be accomplished by treatment of the grafted stationary phase under conditions where the adjustable ionization state monomer is in the state which reverses the charge of the stationary phase. For cation-exchange materials with a zwitterionic adjustable ionization state monomer, the mobile phase should be adjusted such that the pH is at least 2 pH units below the pKa of the zwitterionic monomer. In most cases, pH 0 should be more than sufficient to reverse the charge polarity of the stationary phase. Rinsing the column with pH 0 hydrochloric, nitric or methanesulfonic acid (e.g., one molar) for one hour should be sufficient to remove most if not all of the cationic contaminant. If the cationic contaminant is hydrophobic, incorporation of organic solvent in the cleaning solution will accelerate the removal of the contaminant. Including at least 40% acetonitrile in the presence of one molar acid should be sufficient to quantitatively remove even hydrophobic cationic contaminants from a charge reversible cation-exchange material.

In an analogous fashion, cleaning a charge reversible anion-exchange stationary phase can be accomplished by using conditions that maximize the anionic charge while minimizing the cationic charge of the stationary phase. Generally, treating the column for one hour with one molar sodium hydroxide or potassium hydroxide will quantitatively remove most highly charged anions from the stationary phase. Incorporating 40% acetonitrile in the one molar hydroxide solution will enable removal of hydrophobic highly charged anions from the stationary phase. Examples of such impurities can include humic acid, rosin acids and polyacrylic acid.

Figure 5:
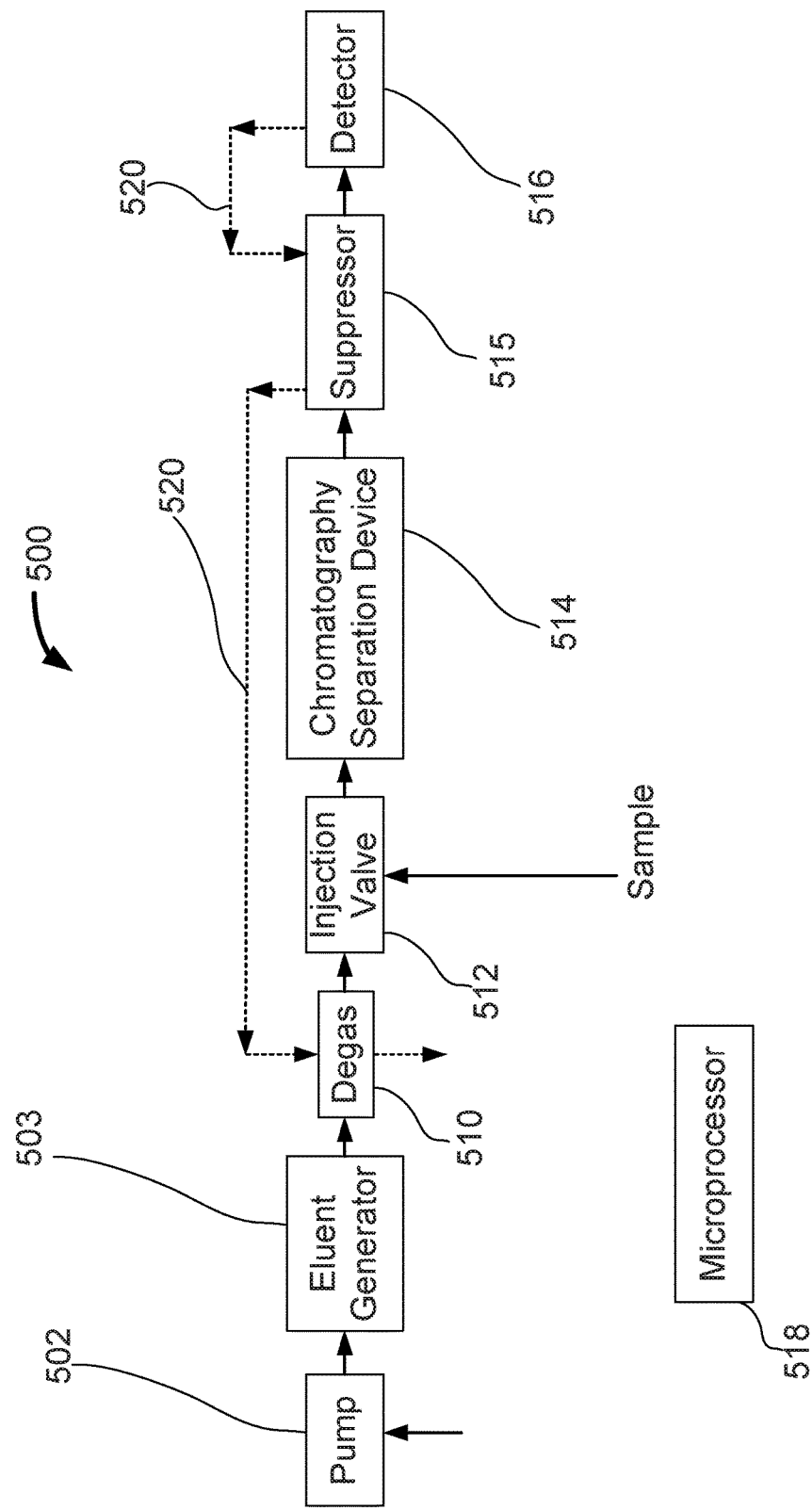
FIG. 5 shows a chromatography system suitable for analyzing ion standards with a chromatography column containing an ion exchange packing material described herein.

Now that the ion exchange chromatographic packing material has been described, the following will describe a general chromatography system suitable for use with the chromatography columns described herein. FIG. 5 illustrates an embodiment of an ion chromatography system 500 that includes a pump 502, an electrolytic eluent generating device 503, a degas assembly 510, an injection valve 512, a chromatography separation device 514, a suppressor 515, a detector 516, and a microprocessor 518. A recycle line 520 may be used to transfer the liquid from an output of detector 516 to a regenerant portion of suppressor 515, and then to an inlet of degas assembly 510.

Pump 502 can be configured to pump a liquid from a liquid source and be fluidically connected to electrolytic eluent generating device 503. Electrolytic eluent generating device 503 is configured to generate an eluent such as for example KOH or methanesulfonic acid. Details regarding electrolytic eluent generating devices (e.g., eluent generator) can be found in U.S. Pat. Nos. 6,225,129 and 6,682,701, which are hereby incorporated by reference herein. In an embodiment, a residual gas may be carbon dioxide, hydrogen, and oxygen. The gas can be swept out of degas assembly 510 using a recycled liquid via a recycle line 520 that is downstream of detector 516. Injection valve 512 can be used to inject an aliquot of a liquid sample into an eluent stream. Chromatography separation device 514 (e.g., chromatography column) can be used to separate various matrix components present in the liquid sample from the analytes of interest. An output of chromatography separation device 514 can be fluidically connected to suppressor 515, and then to detector 516 to measure the presence of the separated chemical constituents of the liquid sample.

Suppressor 515 is a device used in ion chromatography to remove the eluent and sample counterions and replace them with regenerant ions. As a result, the eluent is converted to a weakly dissociated form prior to entering the detector. The suppressor allows analyte ions to be detected with a conductivity detector with a low background. Furthermore, the analytes can be converted to the more conductive acid or base form, which enhances the signal, particularly for fully dissociated species. Detail regarding suppressors can be found in U.S. Pat. Nos. 4,999,098; 6,328,885; and 8,415,168 which are hereby fully incorporated by reference herein.

Detector 516 may be in the form of ultraviolet-visible spectrometer, a fluorescence spectrometer, an electrochemical detector, a conductometric detector, a charge detector, or a combination thereof. Details regarding the charge detector that is based on a charged barrier and two electrodes can be found in US Pre-Grant Publication No. 20090218238, which is hereby fully incorporated by reference herein. For the situation where recycle line 520 is not needed, detector 516 may also be in the form of a mass spectrometer or a charged aerosol detector. The charged aerosol detector nebulizes the effluent flow and creates charged particles that can be measured as a current proportional to the analyte concentration. Details regarding the charged aerosol detector can be found in U.S. Pat. Nos. 6,544,484; and 6,568,245, which are hereby fully incorporated by reference herein.

An electronic circuit may include microprocessor 518 and a memory portion. Microprocessor 518 can be used to control the operation of chromatography system 500. Microprocessor 518 may either be integrated into chromatography system 500 or be part of a personal computer that communicates with chromatography system 500. Microprocessor 518 may be configured to communicate with and control one or more components of chromatography system such as pump 502, electrolytic eluent generating device 503, injection valve 512, and detector 516. Note that chromatography system 500 is a particular machine used to analyze standard solutions and sample solutions to identify chemical constituents and the associated concentration values.

Now that the general chromatography system suitable has been described, the following will describe the use of chromatography columns containing the cation exchange chromatographic packing material of Example 5 with the general chromatography system. FIG. 1 shows a chromatogram of a sample containing 6 cations using a chromatography column containing a cation exchange packing material of Example 5 (described below) using a 2 mM methanesulfonic acid (MSA) eluent. The 6 cation sample contained monovalent ($Li^+$, $Na^+$, $NH_4^+$, and $K^+$) and divalent ions ($Mg^{2+}$, and $Ca^{2+}$). The monovalent ions all co-eluted at around four minutes to form a single peak. The divalent ions eluted at around 13 to 15 minutes to form two distinct peaks. Based on prior experiments, Applicant believes that the elution time was relatively fast for the divalent ions using a relatively low MSA concentration of 2 mM.

Figure 2:
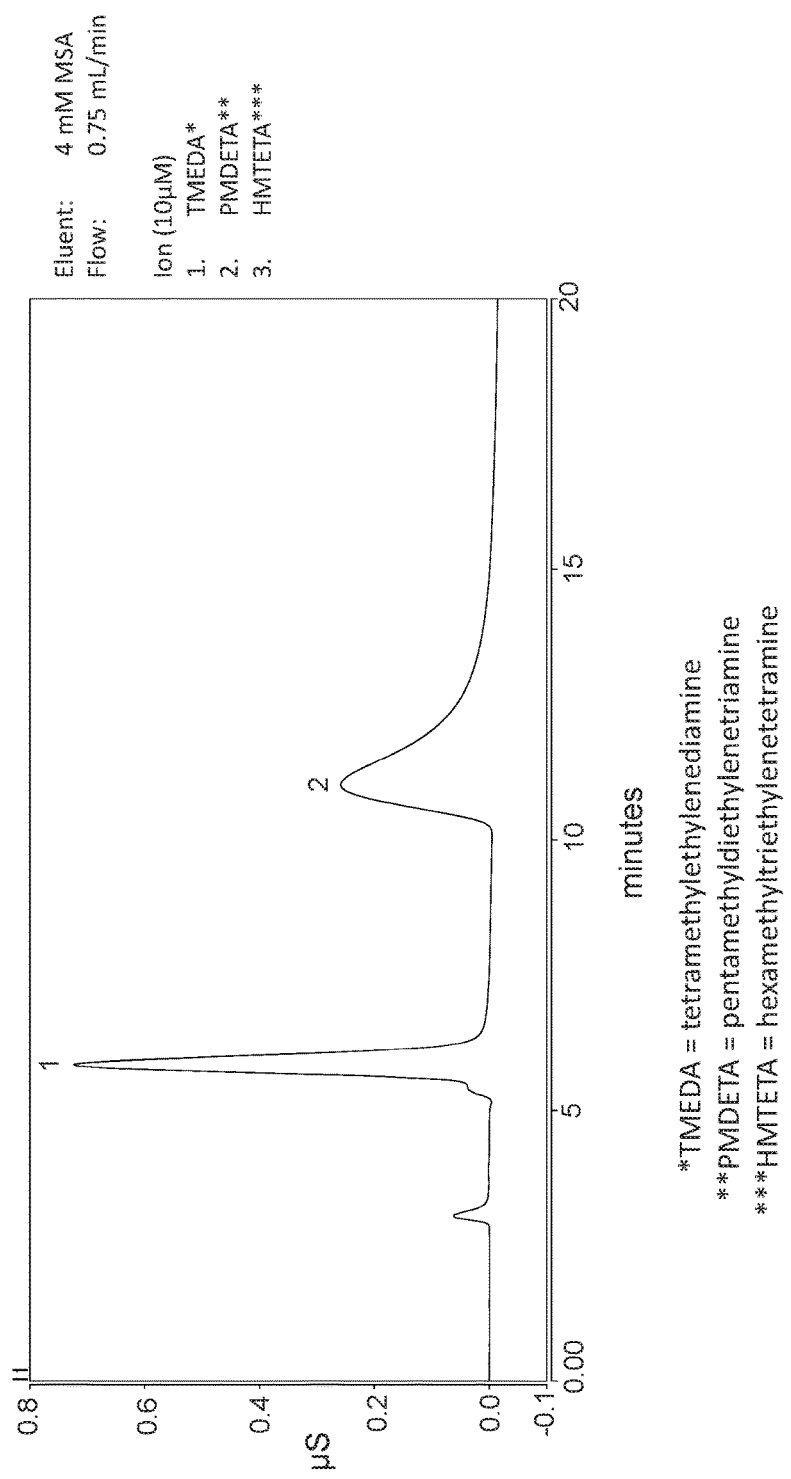
FIG. 2 shows a chromatogram of a sample containing 3 cations using a chromatography column containing a cation exchange packing material of Example 5 using a 4 mM MSA eluent.

FIG. 2 shows a chromatogram of a sample containing 3 cations using a chromatography column containing a cation exchange packing material of Example 5 using a 4 mM MSA eluent. The 3 cation sample contained 10 micromolar each of the following multivalent cations—tetramethylethylenediamine (TMEDA), pentamethyldiethylenetriamine (PMDETA), and hexamethyltriethylenetetramine (HMTETA). At 4 mM MSA, TMEDA is predominantly a divalent cation, PMDETA is predominantly a trivalent cation, and HMTETA is predominantly a tetravalent cation. The divalent ion TMEDA eluted at about 6 minutes. The trivalent ion PMDETA eluted at about 11 minutes. The tetravalent ion HMTETA did not elute within 20 minutes indicating that HMTETA was more strongly bound to the cation exchange packing material that the other two multivalent cations.

Figure 3:
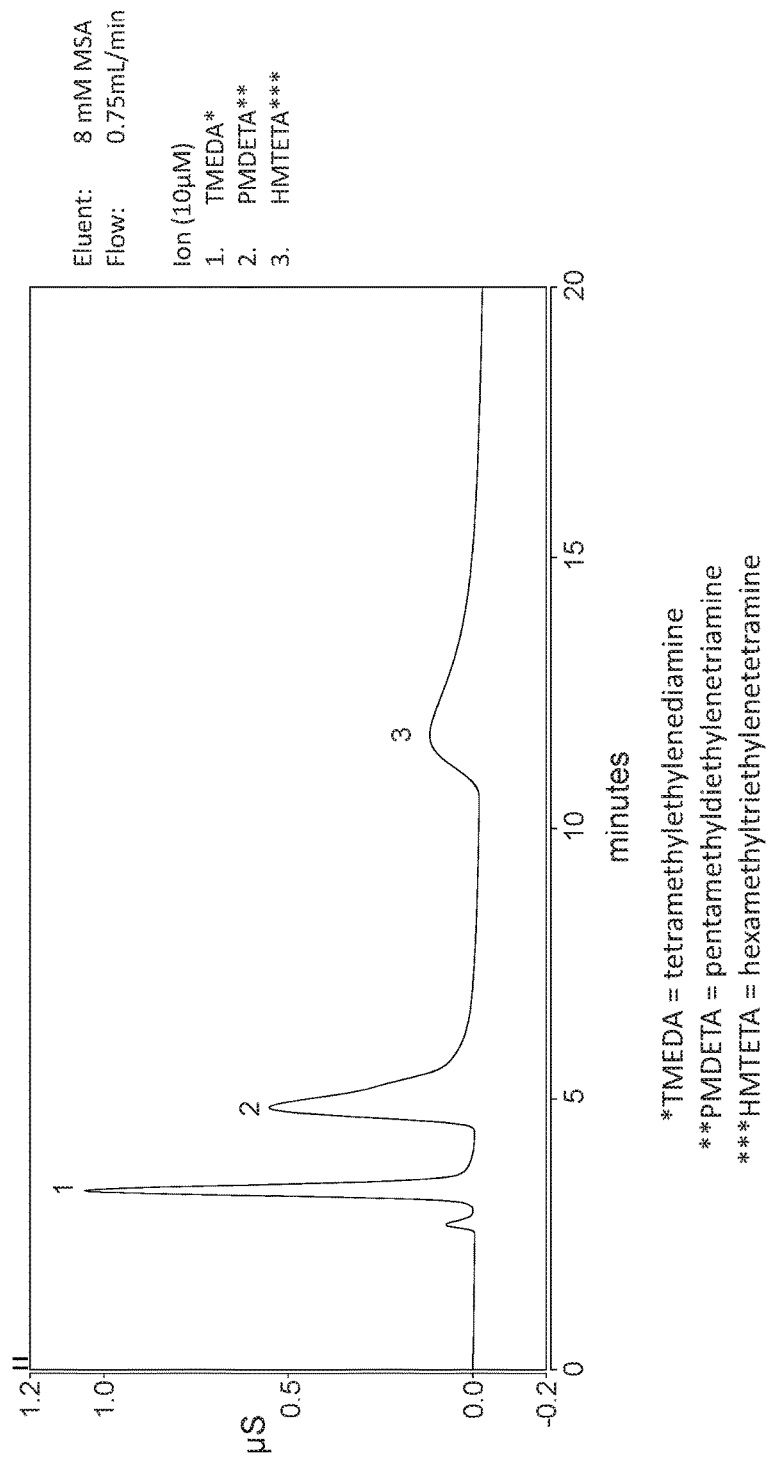
FIG. 3 shows a chromatogram that was performed similar to FIG. 2 except that a higher eluent concentration of 8 mM MSA was used.

FIG. 3 shows a chromatogram that was performed similar to FIG. 2 except that a higher eluent concentration of 8 mM MSA was used. Compared to FIG. 2, the chromatogram of FIG. 3 shows that the tetravalent cation HMTETA did elute faster at about 12 minutes, which is ascribed to the higher eluent concentration of 8 mM MSA.

Figure 4:
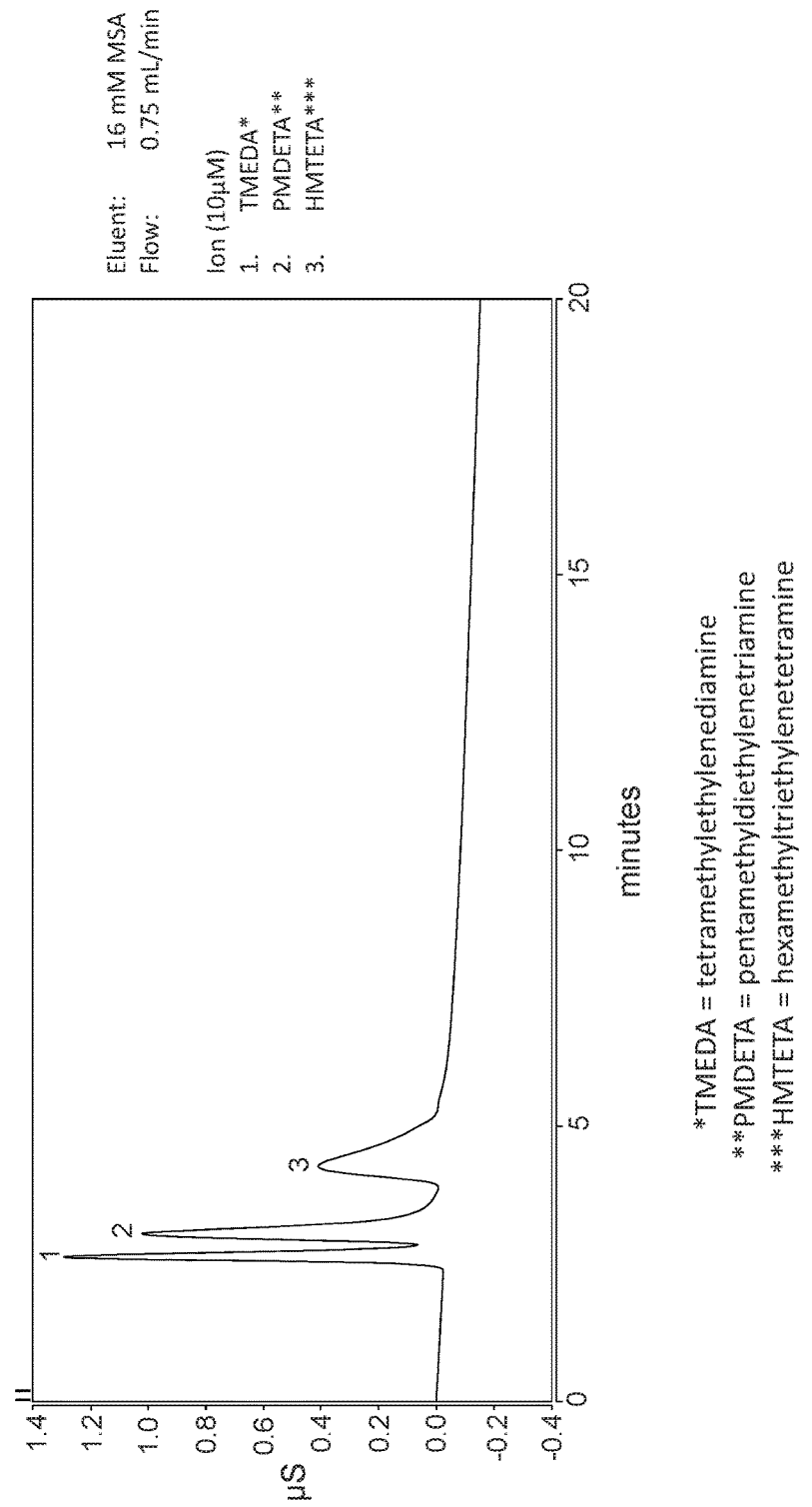
FIG. 4 shows a chromatogram that was performed similar to FIG. 3 except that a higher eluent concentration of 16 mM MSA was used.

FIG. 4 shows a chromatogram that was performed similar to FIG. 3 except that a higher eluent concentration of 16 mM MSA was used. Compared to FIG. 3, the chromatogram of FIG. 4 shows that all of the multivalent cations eluted within 5 minutes, which is ascribed to the higher eluent concentration of 16 mM MSA.

Figure 6:
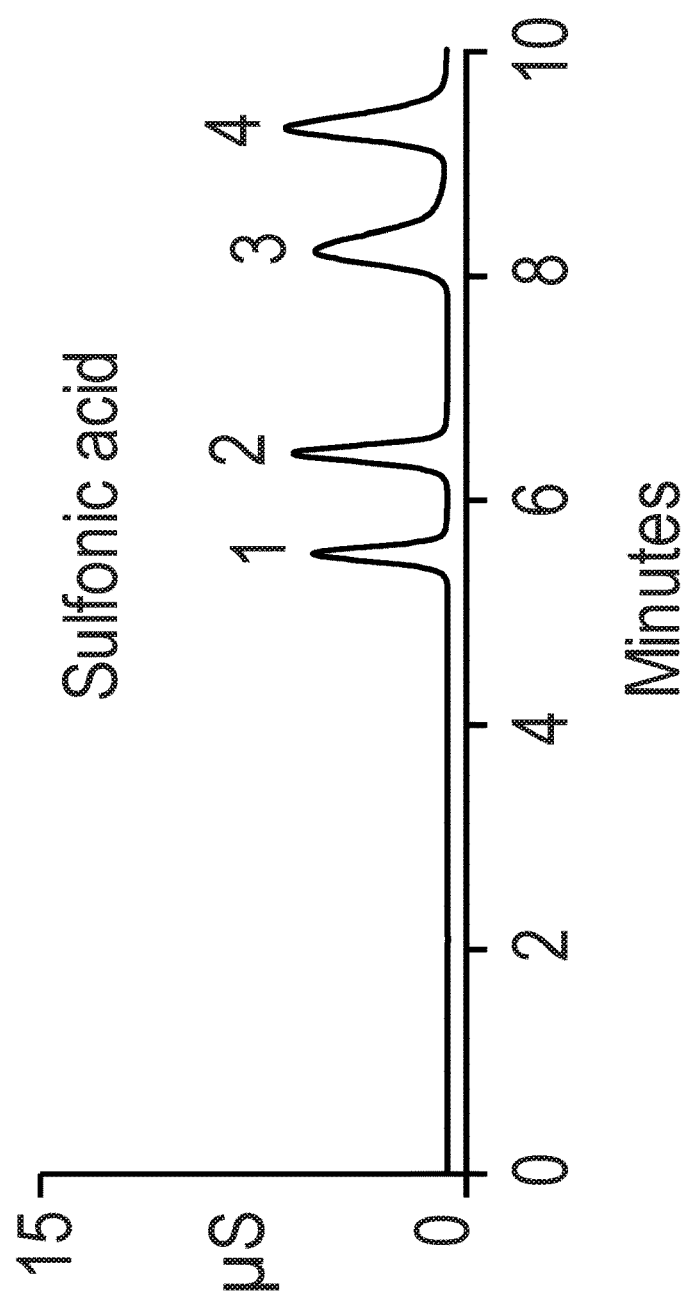
FIG. 6 shows a chromatogram of a sample containing 6 cations using a chromatography column containing a cation exchange packing material of polystyrene sulfonic acid using a 10 mM MSA eluent.

Now that the use of chromatography columns containing the cation exchange chromatographic packing material of Example 5 with the general chromatography system has been described, the following will describe the use a different cation exchange chromatographic packing material. In this embodiment, the cation exchange chromatographic packing material includes a homopolymer of styrene sulfonate tethered to a DVB support particle. FIG. 6 shows a chromatogram of a sample containing 6 cations using a chromatography column containing a cation exchange packing material of polystyrene sulfonic acid using a 10 mM MSA eluent. The 6 cation sample contained monovalent ($Li^+$, $Na^+$, $NH_4^+$, and $K^+$) and divalent ions ($Mg^{2+}$, and $Ca^{2+}$). The monovalent ions all eluted between about 5 minutes to about 10 minutes. The divalent ions did not elute within the 10 minute elution time because the divalent cations were bound more strongly to the cation exchange packing material.

Figure 7:
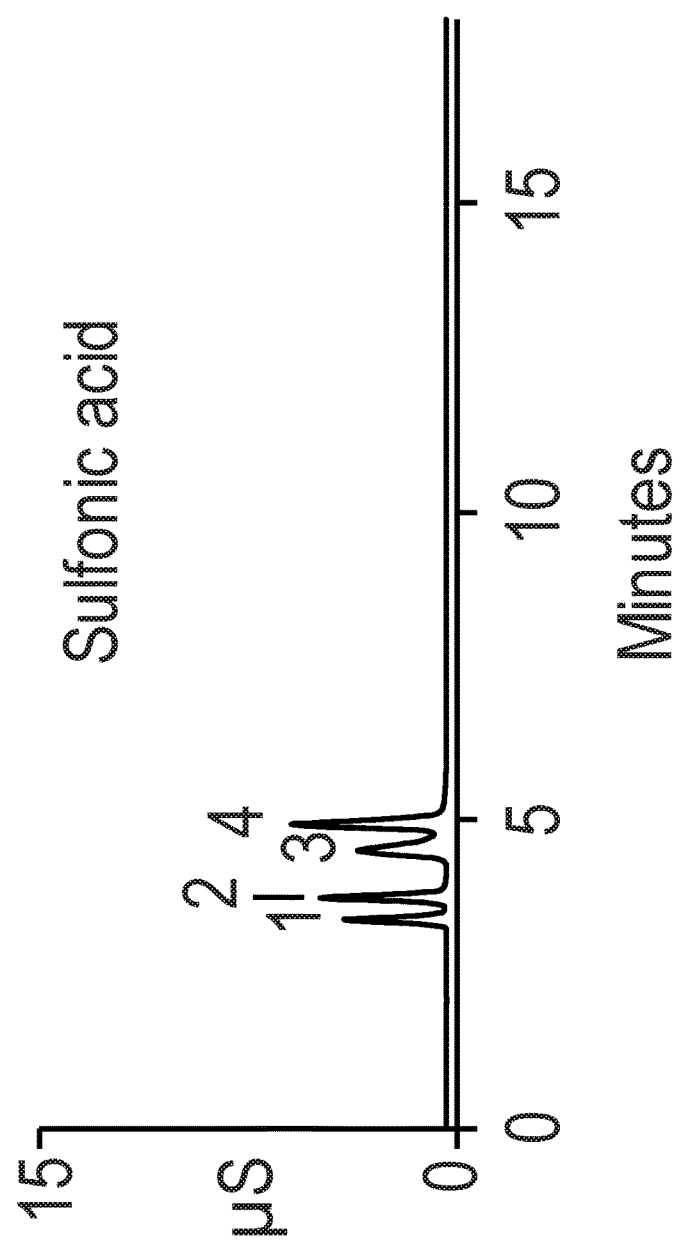
FIG. 7 shows a chromatogram that was performed similar to FIG. 6 except that a higher eluent concentration of 25 mM MSA was used.

FIG. 7 shows a chromatogram that was performed similar to FIG. 6 except that a higher eluent concentration of 25 mM MSA was used. Similar to FIG. 6, the chromatogram of FIG. 7 showed that the monovalent ions all eluted, but with shorter retention times. Even though the chromatogram of FIG. 7 was run longer than the chromatogram of FIG. 6 with a higher MSA concentration, no divalent peaks were observed eluting from the column.

Figure 8:
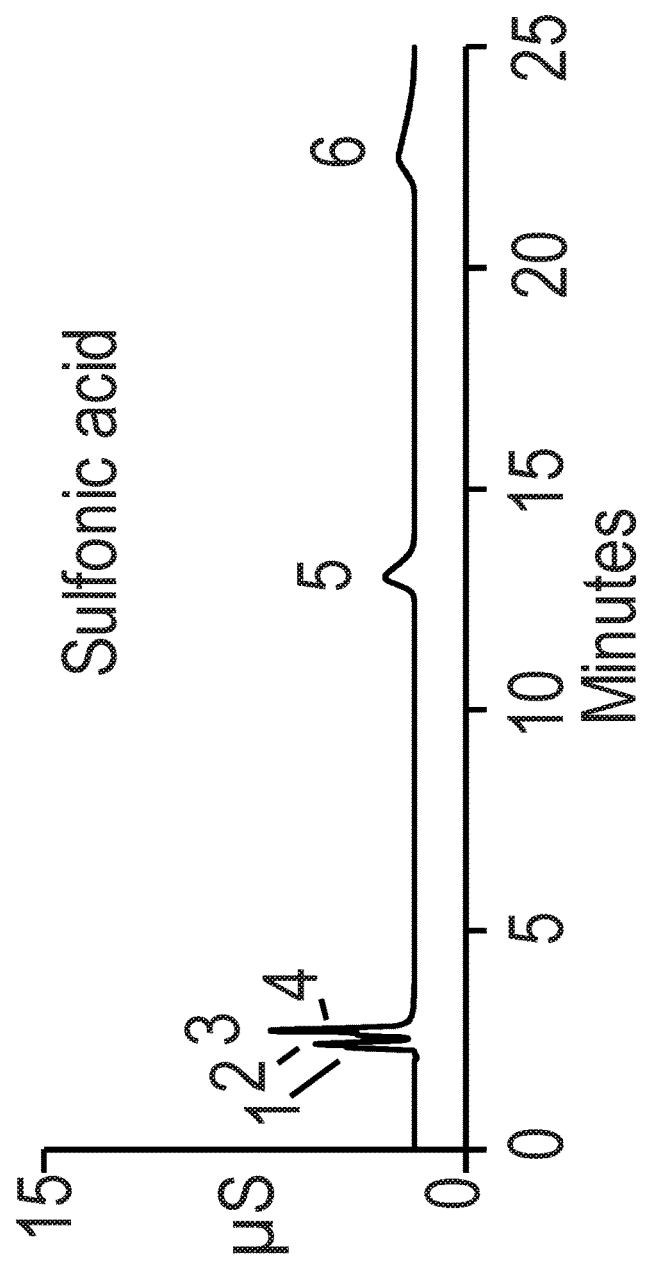
FIG. 8 shows a chromatogram that was performed similar to FIG. 7 except that a higher eluent concentration of 100 mM MSA was used.

FIG. 8 shows a chromatogram that was performed similar to FIG. 7 except that an even higher eluent concentration of 100 mM MSA was used. For this chromatogram, the divalent cations $Mg^{2+}$ and $Ca^{2+}$ eluted at about 13 minutes and 23 minutes. The chromatograms of FIGS. 6 to 8 suggest that relatively high concentrations of eluent (e.g., 100 mM MSA) were needed to elute divalent cations in the 30 minute time frame when using a homopolymer of styrene sulfonate tethered to a DVB support particle. This contrasts to the copolymer of Example 5 as illustrated in FIGS. 1 to 4 where relatively low concentrations of MSA were used (e.g. 16 mM MSA or less) even though styrene sulfonate (a strong cation exchange group) was part of the copolymer. Thus, the use of an adjustable ionization monomer and an ionic crosslinking monomer allowed for preparing sulfonate based cation exchange group resins that can elute cations with relatively modest MSA eluent concentrations within less than about 20 minutes.

Example 1—DVB/EVB Particles

This Example describes the preparation of resin support particle based on divinylbenzene and ethylvinylbenzene, which are referred to as DVB particles. A solution of 20 grams of 75 percent benzoyl peroxide in a mixture of 230 grams (g) of divinylbenzene (containing 55% of actual divinylbenzene) and 230 grams ethylvinylbenzene can be dispersed in the form of fine droplets in 1600 mL of an aqueous solution containing water and 8 grams of polyvinylalcohol (Polysciences Inc. catalog #4398, 125,000 grams/mole, 88% hydrolyzed). The whole mixture can be protected from air by maintaining an atmosphere of nitrogen within the reaction vessel. The mixture can be heated to 80°

C. and held at this temperature for twenty hours during which time polymerization takes place. Liquid can be drained from the resin particles and then can be washed with water to remove water soluble products to yield a white opaque polymer in the form of spherical particles.

Example 2—Vinylbenyzldimethylglycine

This example describes the synthesis of hydrolyzed dimethylglycine ethyl ester (DMGEE) quaternized with vinylbenzyl chloride (VBC), which is an adjustable ionization state monomer, and is referred to as vinylbenyzldimethylglycine (see FIG. 9). 9.955 grams of $H_2O$ was added to a tall form vial (~1" diameter×5" tall). Next, a first portion of 1.962 grams of DMGEE was added to the tall form vial and then stirred to homogenize at room temperature. 10.119 grams VBC was added to the tall form vial and then the tall form vial was placed on a stirrer set to moderate speed. After 4 hours and 44 minutes, a second portion of 2.125 grams of DMGEE was added to the stirred mixture. After about 18 hours from the last addition, a third portion of 2.020 grams of DMGEE was added to the stirred mixture. After about 9 hours from the last addition, a fourth portion of 2.163 grams of DMGEE was added to the stirred mixture. After about 5 days from the last addition, a fifth portion of 1.079 grams of DMGEE was added to the stirred mixture. The reaction mixture became clear after the mixture was mixed for about one more day indicating no visible traces of unreacted VBC. After about 2 days from the last addition, 6.026 g of 50% NaOH was added to the reaction mixture. The reaction mixture became a slightly darker amber color and warm to the touch upon adding the NaOH, but remained a transparent solution. This reaction yields about 0.0663 moles of vinylbenzyldimethylglycine in 35.4 grams or 1.88 millimoles/gram.

Example 3

This example describes the grafting of a copolymer to DVB particles (see FIG. 10) and the subsequent packing into a chromatography column. 4.007 grams of DVB particles from Example 1, 0.613 grams sodium styrene sulfonate, 0.326 grams trimethylvinylbenzylammonium chloride, 1.008 grams of hydrolyzed dimethylglycine ethyl ester quaternized VBC from Example 2, 0.347 grams of V50 initiator (water soluble cationic azo initiator, commercially available from Wako Specialty Chemicals), 0.515 grams 2M $HNO_3$, and 5.096 grams of $H_2O$ were combined in a container and vigorously shaken to homogenize the slurry. Next, the mixture was sonicated for 2 minutes and then the container was put onto a tumbler in a 62° C. oven for 4.75 days. A resin formed in the container as a solid dry mass. Water was added to the container and sonicated to remove the resin. In addition, 20 mL of 1 M sodium acetate was added to the container and sonicated to remove any remaining resin. The sonication liquid was transferred to a specimen cup containing the grafted resin. 100 mL of 1 M sodium acetate was then added to the specimen cup and the slurry was sonicated twice for 1 hour time periods. After this treatment, the resin slurry was still highly flocculated. The slurry was filtered and washed with deionized (DI) water. The resin was then washed twice with 100 mL of 2 M LiCl, 50 mL of DI water, 150 mL acetone and 100 mL of 2 M LiCl, 200 mL of 0.1 M LiCl, and then 200 mL DI $H_2O$. Yield: 10.38 g of damp cake.

5.017 grams of damp cake, 15.241 grams of deionized $H_2O$, and 1.981 grams of 1M acetic acid (HOAc) were combined. The mixture was stirred briefly and then sonicated for 2 minutes. The slurry was topped with deionized $H_2O$ and packed with a pump at 2 mL/min for 60 minutes. The pump reached approximately 2000 pounds per square inch (PSI) in 5 minutes and started to climb slowly at 7.5 minutes. The pressure final pressure was 3365 PSI.

Example 4

This example describes the grafting of a copolymer to DVB particles and the subsequent packing into a chromatography column. 4.015 grams of DVB particles from Example 1, 0.588 grams sodium styrene sulfonate, 0.311 grams trimethylvinylbenzylammonium chloride, 1.004 grams of hydrolyzed dimethylglycine ethyl ester quaternized VBC from Example 2, 0.341 azobiscyanovaleric acid, and 7.484 grams of $H_2O$ were combined in a container and vigorously shaken to homogenize the slurry. Next, the mixture was sonicated for 2 minutes and then the container was put onto a tumbler in a 62° C. oven for about 26 hours. A resin formed in the container as a solid dry mass. Multiple aliquots of about 2 mL of water were added to the container and sonicated to remove the resin. The sonication liquid was transferred to a specimen cup containing the grafted resin. About 10 mL of water was added to the container and then the container was sonicated to remove residual resin from the container walls. This residual resin was transferred to the specimen cup. About 6.6 grams then added to the specimen cup and stirred for one hour followed by sonication for one hour. After this treatment, the resin slurry was still highly flocculated. The slurry was filtered and washed with deionized water. To speed up the washing process, serial aliquots of 30 mL acetone, 30 mL of 1 M HOAc, and then 60 mL of 25% acetone-75% water containing 1 M ammonium acetate was added to the slurry and filtered. The resulting resin was then washed twice with 100 mL of 2 M LiCl and 50 mL of DI water. Yield: 10.504 grams of damp cake.

4.832 grams of damp cake, 19.885 grams of deionized $H_2O$, and 1.025 grams of 1M HOAc were combined. The mixture was stirred 2 minutes and then sonicated for 2 minutes. The resin slurry was transferred to a slurry reservoir with a 4 mm diameter column attached to the reservoir outlet. The slurry was topped with deionized $H_2O$ and then packed using a program that packed at 4 mL/min for 20 minutes. The pump reached the 5400 PSI limit in 4.8 minutes and remained at the pressure limit (of 5400 PSI). The program allowed the flow to remain at a set point (e.g., 4 mL/min) until the specified pressure is reached. After that, the flow rate can drop as needed to maintain constant pressure. The flow rate converged on approximately 2 mL/min. Total packing volume was 45.879 grams.

Example 5—Grafting of Cation Exchange Packing Material and Packing

This example describes the grafting of a copolymer to DVB particles and the subsequent packing of the grafted cation exchange material into a chromatography column. 4.048 grams of DVB particles from Example 1, 0.580 grams sodium styrene sulfonate, 0.308 grams trimethylvinylbenzylammonium chloride, 1.016 grams of hydrolyzed dimethylglycine ethyl ester quaternized VBC from Example 2, 0.362 g V50, 5.990 g 1 M HOAc, and 0.197 grams of $NaClO_4$ were combined in a container and vigorously shaken to homogenize the slurry. Next, the mixture was sonicated for 2 minutes and then the container was put onto a tumbler in a 62° C. oven for about 16 hours. A resin formed in the container as a viscous liquid. Multiple aliquots of about 2 mL of water were added to the container and sonicated to remove the resin. The sonication liquid was transferred to a specimen cup containing the grafted resin. The sonication liquid was stirred for 2-3 minutes and then filtered. The resin was then washed with 2×100 mL of 2 M LiCl, 50 mL of $H_2O$, 100 mL of acetone and 100 mL of $H_2O$. Yield: 10.044 g damp cake.

4.962 grams of damp cake, 17.530 grams of deionized $H_2O$, and 2.704 grams of 1M HOAc were combined. The mixture was stirred 2 minutes and then sonicated for 2 minutes. The resin slurry was transferred to a slurry reservoir with a 4 mm diameter column attached to the reservoir outlet. The slurry was topped with deionized $H_2O$ and then packed using a program that packed at 4 mL/min for 20 minutes. The final pressure at the end of the packing was 3280 PSI. The resulting packing volume was 76.9 grams.

Example 6

The resin of Example 5 was packed into a chromatography column having an inner diameter of 4 millimeters and a length of 250 millimeters. This chromatography column was installed into an ion chromatography system (ICS-2100 commercially available from Thermo Fisher Scientific, Sunnyvale, Calif.) similar to FIG. 5. A pump was used to pump deionized water at a flow rate of about 0.75 mL/min. A Thermo Scientific Dionex capillary EGC 500 MSA cartridge (Thermo Fisher Scientific, Sunnyvale, Calif.) was used for generating MSA eluent at a constant concentration (i.e., isocratic elution). A 2.5 μL injection volume of a cation standard solution was injected into an injection valve. A column heater was used to maintain a column temperature of 30° C. For the chromatogram in FIG. 1, a six cation standard solution contained lithium (2 ppm), sodium (9 ppm), ammonium (4 ppm), potassium (21 ppm), magnesium (9 ppm), and calcium (17 ppm). For the chromatograms in FIGS. 2-4, a three cation standard solution contained a 10 micromolar concentration for each of TMEDA, PMDETA, and HMTETA. For the chromatogram in FIGS. 6-8, a six cation standard solution contained lithium (2 ppm), sodium (5 ppm), ammonium (10 ppm), potassium (10 ppm), magnesium (5 ppm), and calcium (10 ppm). A Dionex 4 mm CERS 300 suppressor was used for autosuppression in the recycle mode. The detector 116 was a Thermo Scientific conductivity detector.

Example 7—Vinylbenzyltetramethylguanidine

This example describes the synthesis of vinylbenzyltetramethylguanidine, which is an adjustable ionization state monomer (see FIG. 11). 15.770 grams of dioxane, 2.192 g of 1,1,3,3-tetramethylguanidine, and 1.577 g of vinylbenzylchloride were mixed at room temperature in a 20 mL vial for approximately two weeks. After several days, reaction product crystals began to accumulate at the bottom of the vial. After approximately two weeks no further crystals were formed. The crystals were filtered and washed with 2×10 mL aliquots of dioxane and allowed to dry in the open air for a few minutes prior to transfer to a vial for storage at room temperature.

Example 8—N-Vinylbenzyl-N,N-dimethyl-N-methylphenol

This example describes the synthesis of N-vinylbenzyl-N,N-dimethyl-N-methylphenol, which is an adjustable ionization state monomer that can be zwitterionic with a quaternary amine and a deprotonated methylphenol group (see FIG. 12). 8.335 g of dioxane, 1.023 g of vinylbenzyldimethylamine, and 1.311 g of p-chloromethylphenylacetate were mixed at room temperature in a 20 mL vial for approximately two weeks. After 24 hours, fine white crystals began to form, coating the walls of the vial. The mixture of fine crystals and dioxane was stirred to produce a homogeneous slurry. A small portion was transferred to another vial containing 10 mL of deionized water. The reaction product was fully soluble in the water.

Example 9—Grafting of Anion Exchange Packing Material and Packing

This example describes the grafting of a copolymer to DVB particles and the subsequent packing of the grafted anion exchange material into a chromatography column. 4.095 grams of DVB particles from Example 1, 0.434 grams sodium styrene sulfonate, 0.329 grams trimethylvinylbenzylammonium chloride, 0.393 grams of vinylbenzyltetramethylguanidine from Example 7, 0.339 g of V50, and 9.791 g of 1 M HOAc were combined in a container and vigorously shaken to homogenize the slurry. Next, the mixture was sonicated for 2 minutes and then the container was put onto a tumbler in a 62° C. oven for about 26 hours. A resin formed in the container as a foamy solid. Water was added to the container to soak the container. A majority of the resin was removed from the container with the aid of a spatula. An additional portion of water was added to the container. By shaking the container, the slurry was transferred to a specimen cup. This process was repeated several times until the majority of the resin was transferred to the specimen cup. Next, 25 mL of methanol was added to the slurry until all floating resin was wetted. The slurry was then filtered through a filter funnel. The resin was filtered to a damp cake and then rinsed 4 times with 10-20 mL DI $H_2O$. The resin was then washed with 2×250 mL of 1M NaCl and 2×25 mL $H_2O$. Yield: 10.980 g damp cake.

5.082 grams of damp cake, 16.032 grams of deionized $H_2O$, and 8.028 grams of 1M HOAc were combined. The mixture was stirred 2 minutes and then sonicated for 2 minutes. The resin slurry was transferred to a slurry reservoir with a 4 mm diameter column attached to the reservoir outlet. The slurry was topped with deionized $H_2O$ and then packed using a program that packed at 4 mL/min for 20 minutes. The pump reached the 5400 PSI limit in 7.1 minutes and remained at the pressure limit (of 5400 PSI). The resulting packing volume was 65.959 grams.

Example 10

The resin of Example 9 was packed into a chromatography column having an inner diameter of 4 millimeters and a length of 250 millimeters. This chromatography column was installed into an ion chromatography system (ICS-2100 commercially available from Thermo Fisher Scientific, Sunnyvale, Calif.) similar to FIG. 5. A pump was used to pump deionized water at a flow rate of about 0.75 mL/min. A Thermo Scientific Dionex capillary EGC 500 KOH cartridge (Thermo Fisher Scientific, Sunnyvale, Calif.) was used for generating KOH eluent at a constant concentration (i.e., isocratic elution). An anion standard solution was injected into an injection valve. A column heater was used to maintain a column temperature of 30° C. A four anion standard solution was tested that contained phosphate, sulfate, and fluoride, and chloride. Table 1 illustrates the retention times (RT) in minutes for a chromatogram at 10 mM hydroxide and 20 mM hydroxide.

TABLE 1

|  | Phosphate (RT) | Sulfate (RT) | Fluoride (RT) | Chloride (RT) |
|---|---|---|---|---|
| 10 mM hydroxide | 1.480 | 1.500 | 1.760 | 3.623 |
| 20 mM hydroxide | 1.577 | 1.577 | 1.750 | 2.750 |

The retention times for fluoride were much less than the retention times for chloride. Increasing the hydroxide concentration significantly reduced the chloride retention, but did not reduce the fluoride retention. Applicant surprisingly observed that the retention times of sulfate and phosphate increased with increasing hydroxide concentration. In addition, another surprising result was that the divalent anions (phosphate and sulfate) eluted before the monovalent anions (fluoride and chloride). A Dionex 4 mm AERS 300 suppressor was used for autosuppression in the recycle mode. The detector 116 was a Thermo Scientific conductivity detector.

While preferred embodiments of the present invention have been shown and described herein, it will be apparent to those skilled in the art that such embodiments are provided by way of example only. Numerous variations, changes, and substitutions will now occur to those skilled in the art without departing from the invention. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. An ion exchange chromatographic packing material comprising:
   a) a support resin particle; and
   b) a copolymer grafted to the support resin particle, the copolymer comprising:
      i) an ion exchange group configured to have a polarity that does not change when switching from use with a first eluent having a first pH to use with a second eluent having a second pH, in which the first pH and the second pH different,
      ii) an ionic crosslinking group configured to ionically bind to the ion exchange group,
      iii) an adjustable ionization state group configured to have a first net charge at the first pH and a second net charge at the second pH, in which the first net charge and the second net charge different,
   wherein an overall first net charge of the chromatographic packing material at the first pH is opposite in polarity to an overall second net charge of the chromatographic packing material at the second pH.

2. The ion exchange chromatographic packing material of claim 1, in which the ion exchange group includes a cation exchange group and the adjustable ionization state group includes a zwitterionic group, in which a mole percent of the ionic crosslinking group is less than a mole percent of the ion exchange group.

3. The ion exchange chromatographic packing material of claim 1, in which the ion exchange group includes a cation exchange group and the adjustable ionization state group includes a zwitterionic group, in which a mole percent of the ionic crosslinking group is less than a mole percent of the adjustable ionization state group.

4. The ion exchange chromatographic packing material of claim 1, in which the ion exchange group includes a cation exchange group and the adjustable ionization state group includes a zwitterionic group, in which a mole summation of the ionic crosslinking group and the adjustable ionization state group is greater than a mole amount of the ion exchange group.

5. The ion exchange chromatographic packing material of claim 4, in which a mole percent of the ion exchange group ranges from about 5% to about 49%, a mole percent of the ionic crosslinking group ranges from about 5% to about 40%, and a mole percent of the adjustable ionization state group ranges from about 10% to about 90%.

6. The ion exchange chromatographic packing material of claim 5, in which the mole percent of the ion exchange group is about 40%, the mole percent of the ionic crosslinking group is about 20%, and the mole percent of the adjustable ionization state group is about 40%.

7. The ion exchange chromatographic packing material of claim 4, in which the ion exchange group includes an anion exchange group, and the first net charge and the overall first net charge have a same polarity.

8. The ion exchange chromatographic packing material of claim 1, in which the ion exchange group includes an ion exchange monomer that has been polymerized, in which the ion exchange monomer is selected from the group consisting of a styrene sulfonate, a vinyltoluene sulfonate, a vinylnaphthalene sulfonate, a 2-sulfoethyl methacrylate, a 3-sulfopropyl methacrylate, a 2-acrylamido-2-methylpropane sulfonate, and combinations thereof.

9. The ion exchange chromatographic packing material of claim 8, in which the ion exchange monomer includes styrene sulfonate.

10. The ion exchange chromatographic packing material of claim 1, in which the ionic crosslinking group includes an ionic crosslinking monomer that has been polymerized, in which the ionic crosslinking monomer is selected from the group consisting of vinylbenzyltrimethylammonium, vinylbenzyldimethylethylammonium, vinylbenzylmethyldiethylammonium, vinylbenzyldimethylethanolammonium, vinylbenzylmethyldiethanolammonium, vinylbenzyltriethylammonium, vinylbenzyltriethanolammonium, vinylbenzyltripropylammonium, 2-acryloxyethyltrimethylammonium chloride, diallyldimethylammonium chloride, 2-methacryloxyethyltrimethylammonium chloride, methacryloylcholine methyl sulfate, and combinations thereof.

11. The ion exchange chromatographic packing material of claim 4, in which the ionic crosslinking group comprises a quaternary amine.

12. The ion exchange chromatographic packing material of claim 10, in which the ionic crosslinking monomer includes vinylbenzyltrimethylammonium.

13. The ion exchange chromatographic packing material of claim 1, in which the adjustable ionization state group includes an adjustable ionization state monomer that has been polymerized, in which the adjustable ionization state monomer is selected from the group consisting of vinylbenzyldimethylglycine, vinylbenzyldimethylaminopropionic acid, vinylbenzyldimethylaminobutyric acid, and combinations thereof.

14. The ion exchange chromatographic packing material of claim 13, in which the adjustable ionization state monomer includes vinylbenzyldimethylglycine.

15. The ion exchange chromatographic packing material of claim 4, in which the zwitterionic group comprises a benzyl group or a dimethylglycine group in which an amine group of the dimethylglycine group is quaternized.

16. The ion exchange chromatographic packing material of claim 15, in which the first net charge of the adjustable ionization state group is neutral and in which the second net charge of the adjustable ionization state group is positive, and wherein the overall second net charge of the chromatographic packing material is positive at the second pH.

17. The ion exchange chromatographic packing material of claim 4, in which the ion exchange group includes a sulfonate group, the ionic crosslinking group includes a quaternary amine group, and the adjustable ionization state group includes a quaternary amine group and a carboxylate group.

18. The ion exchange chromatographic packing material of claim 4, in which the ion exchange group includes a phosphonate group, the ionic crosslinking group includes a quaternary amine group, and the adjustable ionization state group includes a quaternary amine group and a carboxylate group.

19. The ion exchange chromatographic packing material of claim 4, in which the second pH ranges from about 0 to about 1.

20. The ion exchange chromatographic packing material of claim 19, in which the first pH ranges from about 1.5 to about 3.

21. The ion exchange chromatographic packing material of claim 1, in which the copolymer has a linear structure and is tethered to the support resin particle.

22. The ion exchange chromatographic packing material of claim 21, in which the copolymer has a non-uniform distribution of the ion exchange groups, the ionic crosslinking groups, and the adjustable ionization groups.

23. The ion exchange chromatographic packing material of claim 22, in which the copolymer has a first portion proximate to a tethered region where the at least one copolymer is tethered to the support resin particle, in which the copolymer has a second portion proximate to a terminus region of the copolymer, in which a concentration of the ionic crosslinking groups is greater in the second portion than the first portion.

24. The ion exchange chromatographic packing material of claim 23, in which the copolymer includes at least three consecutively bound ionic crosslinking groups in the second portion.

25. The ion exchange chromatographic packing material of claim 1, in which the ion exchange group includes an anion exchange group and the adjustable ionization state group includes a positively charged group, in which a mole percent of the ionic crosslinking group is greater than a mole percent of the ion exchange group.

26. The ion exchange chromatographic packing material of claim 1, in which the ion exchange group includes an anion exchange group and the adjustable ionization state group includes a positively charged group, in which a mole summation of the anion exchange group and the adjustable ionization state group is greater than a mole amount of the ionic crosslinking group.

27. The ion exchange chromatographic packing material of claim 25, in which a mole percent of the ionic crosslinking group ranges from about 20% to about 80%, a mole percent of the ion exchange group ranges from about 5% to about 40%, and a mole percent of the adjustable ionization state group ranges from about 10% to about 90%.

28. The ion exchange chromatographic packing material of claim 27, in which a mole percent of the ionic crosslinking group is about 40%, a mole percent of the ion exchange group is about 30%, and a mole percent of the adjustable ionization state group is about 30%.

29. The ion exchange chromatographic packing material of claim 26, in which the anion exchange group includes a quaternary amine group, the ionic crosslinking group includes a sulfonate group, and the adjustable ionization state group includes a guanidine group.

30. The ion exchange chromatographic packing material of claim 29, in which the first pH ranges from about 11 to about 13, and the second pH ranges from about 13.5 to about 14.5.

31. The ion exchange chromatographic packing material of claim 22, in which the copolymer is tethered to the support resin particle via an unreacted vinyl group at the surface of the support resin particle.

32. The ion exchange chromatographic packing material of claim 1, in which the support resin particle comprises a support copolymer, the support copolymer comprising polymerized support monomers that include: a divinylbenzene and an ethylvinylbenzene.

33. The ion exchange chromatographic packing material of claim 32, in which the support resin particle includes about 55% by weight of divinylbenzene and about 45% by weight of ethylvinylbenzene.

34. The ion exchange chromatographic packing material of claim 33, in which the support resin particle includes a pore size of about 80 angstroms.

35. The ion exchange chromatographic packing material of claim 34, in which the support resin particle includes a surface area of about 450 square meters/gram.

36. The ion exchange chromatographic packing material of claim 35, in which the support resin particle is approximately spherical with a diameter of about seven microns.

37. An ion exchange chromatographic packing material made by a method comprising:
   combining a support resin particle, an ion exchange monomer, an ionic crosslinking monomer, and an adjustable ionization state monomer to form a reaction mixture;
   forming a copolymer of the ion exchange monomer, the ionic crosslinking monomer, and the adjustable ionization state monomer; and
   grafting the copolymer to the support resin particle,
   in which the ion exchange monomer, the ionic crosslinking monomer, and the adjustable ionization state monomer are selected such that the copolymer comprises:
      i) a corresponding ion exchange group configured to have a polarity that does not change when switching from use with a first eluent having a first pH to use with a second eluent having a second pH, in which the first pH and the second pH different,
      ii) a corresponding ionic crosslinking group configured to ionically bind to the ion exchange group,
      iii) a corresponding adjustable ionization state group configured to have a first net charge at the first pH and a second net charge at the second pH, in which the first net charge and the second net charge different, wherein an overall first net charge of the chromatographic packing material at the first pH is opposite in polarity to an overall second net charge of the chromatographic packing material at the second pH, and.

38. The ion exchange chromatographic packing material of claim 37, in which the reaction mixture includes an initiator, an acid, and a perchlorate salt.

* * * * *

UNITED STATES PATENT AND TRADEMARK OFFICE
CERTIFICATE OF CORRECTION

PATENT NO. : 10,379,090 B2
APPLICATION NO. : 15/186258
DATED : August 13, 2019
INVENTOR(S) : Christopher A. Pohl Page 1 of 1

It is certified that error appears in the above-identified patent and that said Letters Patent is hereby corrected as shown below:

In the Claims

Claim 37, Column 25, Line 4: replace "pH, and." with -- pH. --.

Signed and Sealed this
Twelfth Day of November, 2019

Andrei Iancu
*Director of the United States Patent and Trademark Office*